(12) United States Patent
Wu et al.

(10) Patent No.: US 12,410,465 B2
(45) Date of Patent: Sep. 9, 2025

(54) MOLECULAR MARKER COMBINATION LINKED TO QUANTITATIVE TRAITS OF TEA PLANT CAFFEINE CONTENT

(71) Applicant: TEA RESEARCH INSTITUTE, GUANGDONG ACADEMY OF AGRICULTURAL SCIENCES, Guangdong (CN)

(72) Inventors: Hualing Wu, Guangdong (CN); Kaixing Fang, Guangdong (CN); Hongjian Li, Guangdong (CN); Xiaohui Jiang, Guangdong (CN); Dandan Qin, Guangdong (CN); Qiushuang Wang, Guangdong (CN); Chendong Pan, Guangdong (CN); Bo Li, Guangdong (CN)

(73) Assignee: TEA RESEARCH INSTITUTE, GUANGDONG ACADEMY OF AGRICULTURAL SCIENCES, Guangdong (CN)

( * ) Notice: Subject to any disclaimer, the term of this patent is extended or adjusted under 35 U.S.C. 154(b) by 1104 days.

(21) Appl. No.: 17/254,304

(22) PCT Filed: Oct. 14, 2019

(86) PCT No.: PCT/CN2019/110919
§ 371 (c)(1),
(2) Date: Dec. 21, 2020

(87) PCT Pub. No.: WO2021/042448
PCT Pub. Date: Mar. 11, 2021

(65) Prior Publication Data
US 2022/0267835 A1    Aug. 25, 2022

(30) Foreign Application Priority Data

Sep. 4, 2019  (CN) .......................... 201910833668.7
Sep. 4, 2019  (CN) .......................... 201910833687.X
Sep. 4, 2019  (CN) .......................... 201910834185.9

(51) Int. Cl.
*C12Q 1/68*    (2018.01)
*C12Q 1/6827*  (2018.01)

(52) U.S. Cl.
CPC ..... *C12Q 1/6827* (2013.01); *C12Q 2600/156* (2013.01)

(58) Field of Classification Search
None
See application file for complete search history.

(56) References Cited

FOREIGN PATENT DOCUMENTS

| CN | 110468231 | 11/2019 |
| CN | 110760603 | 2/2020 |
| CN | 110819731 | 2/2020 |

OTHER PUBLICATIONS

GenBank Accession AB624028. Jul. 5, 2012 Definition Camellia sinensis DNA, SSR marker, MSG0316, pp. 1-2 (Year: 2012).*
NEB catalog (1996/1997 pp. 111) (Year: 1997).*
Li et al. (Crop Sci. 54:1124-1132 (2014)) (Year: 2014).*
Zhou Chen-Yang, et al., "Nucleotide Acid Diversity of Inosine-5'-monophosphate Dehydrogenase Gene and Association Analysis of the Gene with Caffeine Content in Tea Plant." Acta Horticulturae Sinica, vol. 40, No. 5, Mar. 2013, pp. 981-988.
En-Hua Xia, et al., "Tea Plant Information Archive: a comprehensive genomics and bioinformatics platform for tea plant." Plant Biotechnology Journal, vol. 17, Mar. 2019, pp. 1938-1953.
Zhou, "Molecular Cloning of Inosine-5'-monophosphate Dehydrogenase Gene and Association Analysis of the Gene with Caffeine Content in Tea Plant," Master's thesis, Jun. 2012, Tea Science, Chinese Academy of Agricultural Sciences, pp. 1-62.
Li, "A correlation study of caffeine contents with theobromine contents, transcriptional expression and cSNP of key enzyme genes in tea plants," Master's thesis, Jun. 2013, School of Tea and Food Science, Anhui Agricultural University, pp. 1-53.
Wei, "Cloning of AMP deaminase gene and cSNP analysis of TCS1 in tea plant(*Camellia sinensis*)," Master's thesis, Jun. 2013, School of Tea and Food Science, Anhui Agricultural University, pp. 1-53.

* cited by examiner

*Primary Examiner* — Juliet C Switzer
(74) *Attorney, Agent, or Firm* — JCIP GLOBAL INC.

(57) ABSTRACT

A molecular marker combination linked to quantitative traits of tea plant caffeine content, including a SNP site 1, a SNP site 2, a SNP site 3, a SNP site 4, a SNP site 5 and a SNP site 6, which are located in tea genomes Scaffold4239:309117, Scaffold115:803980, Scaffold720:596655, Scaffold3614:66549, Scaffold349:3413816 and Scaffold920:281727, respectively, and genotypes thereof are extremely significantly correlated with the caffeine content is provided. A detection method for detecting each site, and one or more molecular marker site is used to evaluate the tea plant caffeine content.

1 Claim, 18 Drawing Sheets
Specification includes a Sequence Listing.

Scaffold4239:309117 (as shown in SEQ ID NO:1)

GAAGGCTCTGGAGTAGCTGAAGTTGTTATGAGCTTGTCTAGGCCGAAATCA
GCGAGGTGAGCTTCAAAATCGGCGTCGAATAGGACGTTCTGAGGCTTGAC
ATCGCCATGAACCATGGCGGTGGAGTGGAGGAAGGCGAGGCCGCGGGCGA
TTCCGAGGGCTATTAGGTGGCGCATTGGCCAATTCAATACATGCCCGTCTTG
GTGAGAAGCTTCTTGAAGCAATGTGGCTAGGTTTCCGTTAGGCATATAGTC
GTAGACTAAGAGTCTGAGGTCTGGTGGTCCGGCGAAGTACCCACGGAGGA
CTGTGAGGTTTCTGTGCTTCACTCTCCCGAGCGATTCGGCTTCTTTTCTGAA
CATGTTTTCGTCTAGCGATCCATCAGGGAGTCTCCGAATCGAAAGCACCATT
CCATCACTGTAACAGGCTTT<u>GAAGACTAACCCGTATCGAG</u>TCCTGCTTAG   upstream primer
AACGTTCTCTTCATCGAATTGTCTCGTTGCTTCGGTTGTTTCNGCTAGAGTG   (as shown in SEQ ID NO:2)
ATCTTGTTATTGAACATAACAAGCTTTGGACCGCCATTATCGCCACTTCCAC
GACCTCCGCTGGCTGCAGCTGAGCTTGCTCTTGCTGGGCTGCGCTTTTTCT
CTCCGGCAGCCTTTTCTTTGAGCCTCTTGCGCCA<u>CCGCAAGAGACTGTAA</u>   downstream primer
<u>GTGT</u>AGAAGCAACAACACAGTGCTAAGAGGAAACCACCACTAACAGCCA   (as shown in SEQ ID NO:19)
TGGCAATAAACATGATCAGCCTCTTCTTCCTATTACTCATCTCTTCGCATTTC
GTGCTTAAGGGTTTCCCACATAAGTTCGGATTTCCTGCATAATCAGATGGAT
CGTTGAATCTTGAAGCCAGCATTGTTGGAATCTCGCCGGAGAGGTTGTTTT
GGGATACATTGAAGTAGACCAAGCTAGAGATGAGTGAAATGTTTGCTGGAA
TCGGTCCGGTCAGGTTGTTTGCAGAGAGATTGAGGACTGTGAGGTTTGATA
AATTGGACAATGAGTCTGGTATTTGGCCTGG~

FIG. 2

Scaffold115:803980 (as shown in SEQ ID NO:4)

AATCATTAAGAGTCATTATGGTAATCATGAGCTTAATTACTCCAAGTAAAGC
CAATCTTCATCATAGAAATAAAAATTACAAAAAAAAAAAAAAAAAAAAAAG
TCTTTCAGCTGAACAACCCATCCCTGCAACTGCACCACCATAATTGAGATCT
AAATCTGAAGGAACTTGCTTGAGATCTAAATCTGAAGGAACTTGCTTGCTT
AGGAACATCCACATCCATGATTTCTACAATTTTTGGAAGACACAGAACCAG
AGAAGATGACTCAAAATCAAGCAGCAATTGTAAGAAAATTCGACCAATCG
AAATCATCTTGGAATTAATCATTGTAGCCTC<u>CTTCATCTCCACCACACTTC</u>   upstream primer
TCCTCCTACTTCCATGCGATTACGTCGACGGCAGCCCTATTCCCACCATCATA   (as shown in SEQ ID NO:5)
TTCAAAGGACTCCCCTCCACCTTCCACGCCTTCGTCGTCTCCCTCATCTTCG
CCTTCTCCGGAGCCTTGAGCGCCTTGTTGATCCACGACNCATCCCTCTTTGC
CAAGCTCTGCGAGTTCTCTTCCATGGCCTCCATGACCTCTGCT<u>CTCTCTTT</u>     downstream primer
<u>GCTACTTTGGGC</u>TATGTTCTTCACCTGTTTTCAACCACAACCCAGGTAAAA   (as shown in SEQ ID NO:20)
CTCGAATTCAGACATCACATGGTAAGAAAACAAGTTATTAAGGTTTTTAACC
TTATAAAGACTTTTTTTCTTTTTTCTTTTCCTTCCTGTCCAACGGACACGTGG
TGTGTTTTAAAATTAATAAAATCGTGTATCAGATATGGATATACAATCGCGTGG
TCAGTTGAAATTACTATTGGTATGCTTTATATACCGTGTCGTGTGTAAAATTA
AAACTTGTTTTGTGATGTTGTTGGTCTGTTATGTACTTGGTGTTGTTGAAAT
AATATTACCATAAATTTGAATAAGCCTTTATTATGTGGAGATCCGATGGATTA
ATGATGCATATTGTCACAGAATTCAAAATGATTTCATTTTGAGCATGGTGAC
GAGGGTTCCAAGCCCTG

FIG. 3

Scaffold720:596655 (as shown in SEQ ID NO:7)

GCCCACTAGATAATGGCAAAACCATCTTTTCTAAAGCCCACTTGAGGGTGG

CAAAATCTGCATTTTAGCCTACTTGCGAGTAGCAAACCATTTTCAGAACAA

ACATGAAATGTTTTGTTCCAATTTAGGCGATTTGGTCTACACTTGTTTGCTG

TGCGCATAACATAGTAATTCTAGGCTAATAACCGGAATAAAAGCATATAATG

TTTTCAAAACAAGATATCATGGTTAGTAGAGGCCGATCTTTGATCGGGCGA

GTGGGTATGCTCATAGCTGACCTGCCCCAATTGTACCCAAGTTCCCGAGCC

GAGA<u>CAACTTTGGTGATGACGGAC</u>ACGTGCCCTTTGGCACCGAGTCAGG    upstream primer

GTTTCTTAAATTCTCCCAAAATAAAATATTTAGGTGGCGACTCTGTATCTGG     (as shown in SEQ ID NO:8)

CAAAGCAGTCCATGTTTGGCACTTCTTTTCTAAAAATCTGTTTTCTCAAAAC

AATTTGCCGGATTTGGACTCTTTGGTTCAGATTAAGAACNGTGACAATTCG

AGTCCGAACTGTAGCATGGGGCCCACGGGC<u>GCGTCTACACACCAGTTGA</u>   downstream primer

<u>A</u>GGTAAAGACAGAAGATGTTGAGAAAATTGCATTCAGAGCGAGGTATGGT     (as shown in SEQ ID NO:21)

CATTATGAATTCCTTGTTATGCCATTTGGAGTAACTAATGCCCCTGCAACGTT

TATAGACCTAATGAACTGTATTTTTAAGACTTATCTTGATGATTTTGTTGTGA

TTTTATTAATGATATCTTGGTGTATTCAAAGAATAGACTTGAACATGAACACC

ACTTGAGAACTTTCTTGCAAACACTTAAAGAAAAGAAATTATTTTCCAAAC

TAAAAAAATGTGAATTTTGGTTGGATGAAGTCATTTTCTTAGGGCATGTTAT

CAACAAGGAAGAAATTTCAGTAGATCCACAGAAAATTGAAGCAATTGTGA

ATTGACCCACTCCAACAAATATAACAGAAGTCCATAGTTTCGTGGGCTTAGC

TGGGTACTACAGAAGATTTGTGAAGG-

FIG. 4

Scaffold3614:66549 (as shown in SEQ ID NO:10)

GAGTCATGGGTTTCTTAAATTTCTCTAAAAAATATTTAGGTGGTGACTCTGT
ATCTGGCAAAATAGTCCATTTTTGGCAATTTGATTCAAAATCAGTTTTCCAA
CATATTTGCCGAATTGGGACTTTTTGGTGATTATCTATTTCACATTGCACATG
TGAAATCAGATTCAGAACCGTGGGAGTCCGATACTGTAGGGCTTATTCGTC
TTCCGAAAAGGGGCATGCAAAGTCGAACTACAAGTCCCCTGGGGAGGATG
GATTGCAAAATTACCGTACACAGTAGCAATCCCGTCTTTAAAGGCGTACTTT
ACCAACTGATGGACCATT<u>GATGACACAACCCTCATCTG</u>ATGTAGCCAGGG    upstream primer
TCTTCCCAGTAGTAGATTGAAAGTGTCCGAAACATCCATGACATAGAATTTA    (as shown in SEQ ID NO:11)
ACCTGATGCTCAGACGGGCCGAGTAGGATATGGCTCTTAAACATTACCATG
ACATCTTGGCTCGTATTGTCATATAAGCCTAAACGGCNTGGGTCGTGGGCGT
AAAGTTAGTCGGCCTCACACCGATGGCATAGGCG<u>GTCCTTACCGGGCATA</u>    downstream primer
<u>CATT</u>AATCGCCGATCCGTTATCTACCAACACCACTGGAATCCACTTTTTCTG    (as shown in SEQ ID NO:22)
ACTTTCCAGCGTTACATATAAGGGCCAATTGTGGTTAGCACCCTCAGGTGGT
AACTCTTTATCTATAAAAGATATCACTGGCGTAACATCCCCGGATGTAACCA
ATGATACCAATTGGTCAGCAGTGGTTTCGATAGGGAGTTTGGTCCGGTTCAT
TGCCTCTAGCAGCAGTGCCTGTCTATGCTCCCGAGATGCCATGATTAGCCCC
CAGATTGATATGTCGGCCTGAATCTTCTTAAGCTGTTTCAAGACCAGGTTTT
CTTCAACATCCTTCTCTTTTGATTTCTCGACCCCCACTGTCCTTGATATATGC
CATCTTTTAGGGTTATCACCCATTGGTACCCCTTTCGGTCTAGATTACCCTGA
CTTTAAGGTCTCCTTCTC

FIG. 5

Scaffold349:3413816 (as shown in SEQ ID NO:13)
ATAATCTTTTTGTACTTGTTCAGGTGGAATGAAGCAATCAACCGAGAGTCC
AGGAACATTGAATGCTAGGTCGTCGATCTTCCAAGTCTCCTCCATCCGTGT
GATTGCTGTGCCCGCTCTCAGATTGTCCCCAAATCTTGAGATGATCACACT
TGATTGGCCAGAATGCGCGATCATCGTGCCCTCCACCATCCGATAGTCCTC
GATTTTCGTGCCCATGGTGGTCTCCCAATAGGTAGGGTAGGTTCCGGGGG
ACTGGATTCTGGTGAGGTAAGAGTCCTCTAAATACACTAGCAGACCACTT
CTTTGGCTGAAGTAACCAAACATGACATGCTTGATCA<u>TCTCTGCACTGTT</u>  upstream primer
<u>GTCACTC</u>CGATCGGCTAGGTCCGTCTGATCCGCGGACAATTTCAACACGA  (as shown in SEQ ID NO:14)
AGCAATCGACGCTCAAGATTCGTTTTTCGCCCACGTATTGTGCTAGGGAAA
ACACAGCCGATACAGCCACAGGATCTAGTCCCTGCATAAATAACANTATG
TTTTTTACATAGAGGAAAATAATATCTGTCACATGAATTCTACTCCATTTT
TTAA<u>CCTTCTAAGAAAGTGTGGTG</u>AAAAAAATATTAAATCCATTGGGTA  downstream primer
AAATATAACAGTCTTTAACATAACAATATGGCGAACTATACATTCAATTCT  (as shown in SEQ ID NO:23)
AGAAAATGTCTCATTTTTATAGATTTTTATGAAAGGGATCAACCTTCTTTT
TTTTTATTGGAAGCACTATATAAATAATGTCAAATAGTTTTCCAAACTTAT
CTAAATAAAGTTTTAATAATTTTAATCCACACATTTTGAATTTAATTTACTT
ATTTTTAGTAGATAACATTACCACAGTCAAAAAGAGTGCCAACATGAACC
TCCAGCACACTTGAAGAGCACTTGACGATCATATTGGGAAAGTTACCAGC
CAGCACTCCCAAAAAAAAAAAAAGAAAAAAAGATAAAAGATTAAAAAAA
TTAGTAAAAAGTGACTTTACAAAAAGGAATATTCCACCTCTG

FIG. 6

Scaffold920:281727 (as shown in SEQ ID NO:16)

AGGGAGACTTTTATCTTGAGAGCTAGAAGAAGAGAAAGTTAGAGAAAAGA
AAGAGAAGTAGGAAGAAAATCAAAGGGAATTCACATTCGTCCTTTTGGAG
TTGAGAATTGAACACTTAGGTGATTTCGAAAATCATAAATGAGGTGTGTTA
AACTAATATCGTTCAGCTACAGTTACTCAGTAAATTCTCTTTCTCAGAGGCT
ACGCAGGTGTAGTTTGAGTTAAACTTGGCCACTTAAACTAATGGAACCATT
AGGGGCCCAAGCTAATTAGTTCCTAGAACAAAGGAGAGAGGACGGAGAA
GCATAGAGAAAGTTAGAGAGAAACTTTTTTCTTGAGAGATAGAAGAGATAG
TTAGAGAAAAGAAAGAGAAACGGGAAAAAAATCATTGGGAA<u>TTCGCATT</u>   upstream primer
<u>CGTCCTTTTGGG</u>CTTGAGAATTGAACAGTTGGGGAATTTGGGAAACCTTA   (as shown in SEQ ID NO:17)
AATGCGGTGCTTATGTTTAACTAATATCGTTAAGTGCCAATTACTCANTAAAT
CCTCTTTCTTAGATGCTAAGCAAGATTTAGTGTAGTTAAACTTGGCCACTTA
AGCTAATGGAACAGTTAGGGTCCCAAGCGAATTAGTTTCCTAGAACAAAAG
ATAGAA<u>GGATGGAGAATGTAGCACGT</u>TCGTGAGGGACCCCGCTACTACA   downstream primer
GTTCGGACTCGATTTGTGTCACGGTTCTTAATCTGAACCAAAGAGTCCAAA   (as shown in SEQ ID NO:24)
TCCGGCAAATCGTTTTGAGAAACAGATTTTTTGAAAAGAAGTGCCAAACAT
GGACTGCTTTGCTAGATATAGAGTCGCCACCTAAATATTTTTTTAAAATGGG
GAAATTTAGGAAACCCTAACTTGGTGCCAAAGGCCACGTGTCCGTCATTGC
CAAAGTTGCCTGGGCTCGGGAGCTTGGGTACGATTGGGGAAGGTCAGCTAT
GAGCACCCCTCTCGCCCGATCCGAAGATCGGCCTCTACTAACCGTGATATC
CGTTTTTGAAAACGTTATGTGTTCTTAAACCAATT

FIG. 7

MOLECULAR MARKER COMBINATION LINKED TO QUANTITATIVE TRAITS OF TEA PLANT CAFFEINE CONTENT

CROSS-REFERENCE TO RELATED APPLICATION

This application is a 371 of international application of PCT application serial no. PCT/CN2019/110919, filed on Oct. 14, 2019, which claims the priority benefit of China application no. 201910833687.X, China application no. 201910834185.9, and China application no. 201910833668.7, filed on Sep. 4, 2019. The entirety of each of the above mentioned patent applications is hereby incorporated by reference herein and made a part of this specification.

TECHNICAL FIELD

The present invention relates to the technical field of molecular genetics and breeding, and more specifically, to a molecular marker combination linked to quantitative traits of tea plant caffeine content.

BACKGROUND

Tea (Camellia sinensis (L.) O.Kuntze) belongs to the genus Camellia (Theaceae), which originated in southwest China, with a cultivation history of more than 5,000 years. Tea, coffee, and cocoa are collectively referred to as the world's three major non-alcoholic beverages, which have important economic value and have an important impact on society and culture.

Caffeine, which is a characteristic secondary metabolite in tea shoots, is one of the main factors affecting tea flavor. Caffeine is a high content of alkaloids in tea, generally 2% to 5%. Each cup of 150 ml tea soup contains about 40 mg of caffeine. Caffeine is a central nervous system stimulant, so it has a refreshing effect. In addition, caffeine also has the effect of enhancing physical strength, perseverance and endurance. Studies have shown that caffeine can enhance muscle energy, especially for upper limb muscles. Caffeine can also promote metabolism.

Ingesting 200 mg of caffeine, the metabolism rate will increase by 7% in the next 3 hours, and the rate of fat burning will be greatly improved. Caffeine can help relieve pain, because it can accelerate the onset of other pain medications. Caffeine has the effect of improving antioxidation, and caffeine can double the effectiveness of antioxidant phenolics.

However, some people are very sensitive to caffeine, even a small amount of caffeine intake can cause severe insomnia, rapid heartbeat, and increased blood pressure, and the risk of myocardial infarction after intake of excessive caffeine is higher.

Existing research shows that caffeine varies from different producing area and different varieties. In order to meet the needs of different populations, tea plants with different caffeine content need to be cultivated. Meanwhile, due to the importance of caffeine to tea quality and physiological functions, it is of great significance to breed tea plant varieties with specific caffeine content. At present, tea plant breeding is mainly adopt conventional methods, that is, excellent individual plants are selected from wild populations and hybrid offspring for systematic breeding. This method is time-consuming and inefficient, which makes the replacement of new varieties slow, and it cannot quickly meet the public's demand for new products. Since molecular marker-assisted breeding can select breeding materials at the seedling stage, it can significantly improve breeding efficiency. The discovery of molecular markers that are closely linked to the excellent traits of the tea plant is the basis for the molecular marker-assisted selective breeding of tea plant.

SUMMARY OF THE INVENTION

Objectives of the present invention are to overcome the shortcomings of the prior art and provide a molecular marker combination linked to quantitative traits of tea plant caffeine content.

The first objective of the present invention is to provide a molecular marker combination linked to quantitative traits of tea plant caffeine content. The molecular marker combination comprises a SNP site 1, a SNP site 2, a SNP site 3, a SNP site 4, a SNP site 5 and a SNP site 6, which are located in tea genomes Scaffold4239:309117, Scaffold115:803980, Scaffold720:596655, Scaffold3614:66549, Scaffold349:3413816 and Scaffold920:281727, respectively, which are a 501st base of a nucleotide sequence shown in SEQ ID NO: 1, a 501st base of a nucleotide sequence shown in SEQ ID NO: 4, a 501st base of a nucleotide sequence shown in SEQ ID NO: 7, a 501st base of a nucleotide sequence shown in SEQ ID NO: 10, a 501st base of a nucleotide sequence shown in SEQ ID NO: 13, and a 501st base of a nucleotide sequence shown in SEQ ID NO: 16.

The second objective of the present invention is to provide use of any one or more molecular markers of the molecular marker combination in evaluating the tea plant caffeine content.

The third objective of the present invention is to provide use of primers of any one or more molecular markers of the molecular marker combination in evaluating the tea plant caffeine content.

The fourth objective of the present invention is to provide primers for detecting SNP site 1.

The fifth objective of the present invention is to provide primers for detecting SNP site 2.

The sixth objective of the present invention is to provide primers for detecting SNP site 3.

The seventh objective of the present invention is to provide primers for detecting SNP site 4.

The eighth objective of the present invention is to provide primers for detecting SNP site 5.

The ninth objective of the present invention is to provide primers for detecting SNP site 6.

The tenth objective of the present invention is to provide a kit for evaluating tea plant caffeine content.

The eleventh objective of the present invention is to provide a method for evaluating tea plant caffeine content.

The twelfth objective of the present invention is to provide use of one or more of any one or more molecular markers of the molecular marker combination, the primers for the SNP site 1, the primers for the SNP site 2, the primers for the SNP site 3, the primers for the SNP site 4, the primers for the SNP site 5, the primers for the SNP site 6, or the kit in molecular-assisted breeding.

In order to achieve the above objectives, the present invention is realized by the following technical solutions:

After a long period of exploratory research, the inventors discovered six SNP site molecular markers linked to caffeine content. It is further used to establish a detection method for detecting the sites, which can be used to evaluate the tea plant caffeine content, for further use in resource screening and molecular breeding.

Therefore, the present invention claims a molecular marker combination linked to quantitative traits of tea plant caffeine content, including a SNP site 1, a SNP site 2, a SNP site 3, a SNP site 4, a SNP site 5 and a SNP site 6, which are located in tea genomes Scaffold4239: 309117, Scaffold115: 803980, Scaffold720:596655, Scaffold3614:66549, Scaffold349:3413816 and Scaffold920:281727, respectively, i.e., a 501st base of a nucleotide sequence shown in SEQ ID NO: 1, a 501st base of a nucleotide sequence shown in SEQ ID NO: 4, a 501st base of a nucleotide sequence shown in SEQ ID NO: 7, a 501st base of a nucleotide sequence shown in SEQ ID NO: 10, a 501st base of a nucleotide sequence shown in SEQ ID NO: 13, and a 501st base of a nucleotide sequence shown in SEQ ID NO: 16.

The SNP site 1 is located in the tea genome Scaffold4239: 309117 (i.e. the 501st base of the nucleotide sequence shown in SEQ ID NO: 1), this site is G or A, and genotype thereof is extremely significantly correlated with the caffeine content in the dry matter of the tea plant. It is shown by correlation analysis and significance analysis verification that the tea plant caffeine content in the dry matter of tea soup corresponding to an AA genotype sample has extremely significant difference compared with GG and GA genotype samples. It is statistically judged that, when the genotype of the sample is double mutant AA, the caffeine content in the dry matter in the tea plant is more likely to be lower than the normal average of the sample of which the genotype is wild type GG or single mutant GA.

The SNP site 2 is located in the tea genome Scaffold115: 803980 (i.e. the 501st base of the nucleotide sequence shown in SEQ ID NO: 4), this site is G or A, and genotype thereof is extremely significantly correlated with the caffeine content in the dry matter of the tea plant. It is shown by correlation analysis and significance analysis verification that the caffeine content in the dry matter of the tea plant corresponding to a GG genotype sample has extremely significant difference compared with AA and GA genotype samples. It is statistically judged that, when the genotype of the sample is double mutant GG, the caffeine content in the dry matter in the tea plant is more likely to be lower than the sample of which the genotype is wild type AA or single mutant GA.

The SNP site 3 is located in the tea genome Scaffold720: 596655 (i.e. the 501st base of the nucleotide sequence shown in SEQ ID NO: 7), this site is T or C, and genotype thereof is extremely significantly correlated with the caffeine content in the dry matter of the tea plant. It is shown by correlation analysis and significance analysis verification that the caffeine content in the dry matter of the tea plant corresponding to a CC genotype sample has extremely significant difference compared with a CT genotype sample. It is statistically judged that, when the genotype of the sample is single mutant CT, the caffeine content in the dry matter in the tea plant is more likely to be lower than the normal average of the CC type.

The SNP site 4 is located in the tea genome Scaffold3614: 66549 (i.e. the 501st base of the nucleotide sequence shown in SEQ ID NO: 10), this site is C or T, and genotype thereof is extremely significantly correlated with the caffeine content in the dry matter of the tea plant. It is shown by correlation analysis and significance analysis verification that the caffeine content in the dry matter of tea soup corresponding to a CC genotype sample has extremely significant difference compared with TT and CT genotype samples. It is statistically judged that, when the genotype is double mutant CC, the caffeine content in the dry matter in the tea plant is more likely to be lower than the normal average of the sample of which the genotype is wild type TT or single mutant CT.

The SNP site 5 is located in the tea genome Scaffold349: 3413816 (i.e. the 501st base of the nucleotide sequence shown in SEQ ID NO: 13), this site is G or A, and genotype thereof is extremely significantly correlated with the caffeine content in the dry matter of the tea plant. It is shown by correlation analysis and significance analysis verification that the caffeine content in the dry matter of tea soup corresponding to a GG genotype sample has extremely significant difference compared with GA and AA genotype samples. It is statistically judged that, when the genotype is double mutant GG, the caffeine content in the dry matter in the tea plant is more likely to be lower than the normal average of the sample of which the genotype is wild type AA or single mutant GA.

The SNP site 6 is located in the tea genome Scaffold920: 281727 (i.e. the 501st base of the nucleotide sequence shown in SEQ ID NO: 16), this site is G or A, and genotype thereof is extremely significantly correlated with the caffeine content in the dry matter of the tea plant. It is shown by correlation analysis and significance analysis verification that the caffeine content in the dry matter of tea soup corresponding to a GG genotype sample has extremely significant difference compared with GA and AA genotype samples. It is statistically judged that, when the genotype is double mutant GG, the caffeine content in the dry matter in the tea plant is more likely to be lower than the normal average of the sample of which the genotype is wild type AA or single mutant GA.

The tea plant caffeine content according to the present invention is specifically a proportion of caffeine in dry matter of fresh tea leaves.

Use of any one or more molecular markers of the molecular marker combination in evaluating the tea plant caffeine content also belongs to the scope of protection of the present invention.

The present invention further claims use of primers of any one or more molecular markers of the molecular marker combination in evaluating the tea plant caffeine content.

Primers for the SNP site 1, wherein nucleotide sequences thereof are shown as SEQ ID NO: 2 and SEQ ID NO: 3.

```
primer F:
                                    (SEQ ID NO: 2)
GAAGACTAACCCGTATCGAG;

primer R:
                                    (SEQ ID NO: 3)
ACACTTACAGTCTCTTGCGG.
```

Primers for the SNP site 2, wherein nucleotide sequences thereof are shown as SEQ ID NO: 5 and SEQ ID NO: 6.

```
primer F:
                                    (SEQ ID NO: 5)
CTTCATCTCCACCACACTTC;

primer R:
                                    (SEQ ID NO: 6)
GCCCAAAGTAGCAAAGAGAG.
```

Primers for the SNP site 3, wherein nucleotide sequences thereof are shown as SEQ ID NO: 8 and SEQ ID NO: 9.

```
primer F:
                            (SEQ ID NO: 8)
CAACTTTGGTGATGACGGAC;

primer R:
                            (SEQ ID NO: 9)
TTCAACTGGTGTGTAGACGC.
```

Primers for the SNP site 4, wherein nucleotide sequences thereof are shown as SEQ ID NO: 11 and SEQ ID NO: 12.

```
primer F:
                            (SEQ ID NO: 11)
GATGACACAACCCTCATCTG;

primer R:
                            (SEQ ID NO: 12)
AATGTATGCCCGGTAAGGAC.
```

Primers for the SNP site 5, wherein nucleotide sequences thereof are shown as SEQ ID NO: 14 and SEQ ID NO: 15.

```
primer F:
                            (SEQ ID NO: 14)
TCTCTGCACTGTTGTCACTC;

primer R:
                            (SEQ ID NO: 15)
CACCACACTTTCTTAGAAGG.
```

Primers for the SNP site 6, wherein nucleotide sequences thereof are shown as SEQ ID NO: 17 and SEQ ID NO: 18.

```
primer F:
                            (SEQ ID NO: 17)
TTCGCATTCGTCCTTTTGGG;

primer R:
                            (SEQ ID NO: 18)
ACGTGCTACATTCTCCATCC.
```

Further, the present invention claims a kit for evaluating tea plant caffeine content, including a reagent for detecting the molecular marker combination or any one molecular marker thereof.

Preferably, the reagent is the primers for the SNP site 1 which have the nucleotide sequences shown as SEQ ID NO: 2 and SEQ ID NO: 3, the primers for the SNP site 2 which have the nucleotide sequences shown as SEQ ID NO: 5 and SEQ ID NO: 6, the primers for the SNP site 3 which have the nucleotide sequences shown as SEQ ID NO: 8 and SEQ ID NO: 9, the primers for the SNP site 4 which have the nucleotide sequences shown as SEQ ID NO: 11 and SEQ ID NO: 12, the primers for the SNP site 5 which have the nucleotide sequences shown as SEQ ID NO: 14 and SEQ ID NO: 15, and/or the primers for SNP site 6 which have the nucleotide sequences shown as SEQ ID NO: 17 and SEQ ID NO: 18.

The most preferably, the kit contains the primers for the SNP site 1 which have the nucleotide sequences shown as SEQ ID NO: 2 and SEQ ID NO: 3, the primers for the SNP site 2 which have the nucleotide sequences shown as SEQ ID NO: 5 and SEQ ID NO: 6, the primers for the SNP site 3 which have the nucleotide sequences shown as SEQ ID NO: 8 and SEQ ID NO: 9, the primers for the SNP site 4 which have the nucleotide sequences shown as SEQ ID NO: 11 and SEQ ID NO: 12, the primers for the SNP site 5 which have the nucleotide sequences shown as SEQ ID NO: 14 and SEQ ID NO: 15, the primers for the SNP site 6 which have the nucleotide sequences shown as SEQ ID NO: 17 and SEQ ID NO: 18, 2×Taq PCR Master Mix, and ddH$_2$O.

A usage method is as follows:

(1) CTAB method is used to extract total DNA from buds of tea plant, it is ensured that A260/A280 of each DNA sample is between 1.8 and 2.0, and the concentration is greater than 100 μg/μl;

(2) PCR Amplification

PCR system (10 μl) is as follows:

| 2× Taq PCR Master Mix | 5 μl |
|---|---|
| primer | Each 0.5 μl |
| DNA template | 1 μl |
| ddH$_2$O | 3 μl |

PCR amplification procedure is as follows:

| 95° C. | 5 minutes | |
|---|---|---|
| 95° C. | 30 seconds | ×45 cycles |
| 56° C. | 30 seconds | |
| 72° C. | 30 seconds | |
| 72° C. | 2 minutes | |
| 4° C. | forever | |

(3) Product Purification

The PCR amplification products are subjected to gel electrophoresis, followed by recovery and purification using a commercially available gel electrophoresis DNA recovery kit.

A band with a fragment length of about 240 bp in the amplification product of the primers shown in SEQ ID NO: 2 and SEQ ID NO: 3 is selected for recovery and purification.

A band with a fragment length of about 240 bp in the amplification product of the primers shown in SEQ ID NO: 5 and SEQ ID NO: 6 is selected for recovery and purification.

A band with a fragment length of about 250 bp in the amplification product of the primers shown in SEQ ID NO: 8 and SEQ ID NO: 9 is selected for recovery and purification.

A band with a fragment length of about 240 bp in the amplification product of the primers shown in SEQ ID NO: 11 and SEQ ID NO: 12 is selected for recovery and purification.

A band with a fragment length of about 240 bp in the amplification product of the primers shown in SEQ ID NO: 14 and SEQ ID NO: 15 is selected for recovery and purification.

A band with a fragment length of about 240 bp in the amplification product of the primers shown in SEQ ID NO: 17 and SEQ ID NO: 18 is selected for recovery and purification.

(4) Sequencing and Interpretation of Results

The recovered and purified product is sent to a sequencing company for Sanger sequencing. At the site Scaffold4239:309117, it is statistically judged that, when the genotype sample is double mutant AA, the caffeine content in the dry matter in the tea plant is more likely to be lower than the normal average of the sample of which the genotype is wild type GG or single mutant GA.

At the site Scaffold115:803980, it is statistically judged that, when the genotype of the sample is double mutant GG, the caffeine content in the dry matter in the tea plant is more likely to be lower than the normal average of the sample of which the genotype is wild type AA or single mutant GA.

At the site Scaffold720:596655, it is statistically judged that, when the genotype is single mutant CT, the caffeine content in the tea plant is more likely to be lower than the normal average of the sample of which the genotype is CC.

At the site Scaffold3614:66549, it is statistically judged that, when the genotype is double mutant CC, the caffeine content in the dry matter in the tea plant is more likely to be lower than the normal average of the sample of which the genotype is wild type TT or single mutant CT.

At the site Scaffold349:3413816, it is statistically judged that, when the genotype is double mutant GG, the caffeine content in the dry matter in the tea plant is more likely to be lower than the normal average of the sample of which the genotype is wild type AA or single mutant GA.

At the site Scaffold920:281727, it is statistically judged that, when the genotype is double mutant GG, the caffeine content in the dry matter in the tea plant is more likely to be lower than the normal average of the sample of which the genotype is wild type AA or single mutant GA.

In the meantime, the present invention claims a method for evaluating the tea plant caffeine content, which detects a genotype of any one or more molecular markers of the molecular marker combination.

Use of any one or more of any one or more molecular markers of the molecular marker combination, the primers for the SNP site 1, the primers for the SNP site 2, the primers for the SNP site 3, the primers for the SNP site 4, the primers for the SNP site 5, the primers for the SNP site 6 or the kit in molecular-assisted breeding.

Compared with the prior art, the present invention has the following beneficial effects.

The present invention first discovered a molecular marker combination linked to quantitative traits of tea plant caffeine content, which includes a SNP site 1, a SNP site 2, a SNP site 3, a SNP site 4, a SNP site 5 and a SNP site 6, which are located in tea genomes Scaffold4239:309117, Scaffold115:803980, Scaffold720:596655, Scaffold3614:66549, Scaffold349:3413816 and Scaffold920:281727, and genotypes thereof are all extremely significantly correlated with the caffeine content.

The SNP site 1 is located in the tea genome Scaffold4239:309117, this site is G or A, and genotype thereof is extremely significantly correlated with the caffeine content in dry matter of the tea plant. It is shown by correlation analysis and significance analysis verification that the tea plant caffeine content in the dry matter of tea soup corresponding to an AA genotype sample has extremely significant difference compared with GG and GA genotype samples. It is statistically judged that, when the genotype sample is double mutant AA, the caffeine content in the dry matter in the tea plant is more likely to be lower than the normal average of the sample of which the genotype is wild type GG or single mutant GA.

The SNP site 2 is located in the tea genome Scaffold115:803980, this site is G or A, and genotype thereof is extremely significantly correlated with the caffeine content in the dry matter of the tea plant. It is shown by correlation analysis and significance analysis verification that the caffeine content in the dry matter of the tea plant corresponding to a GG genotype sample has extremely significant difference compared with AA and GA genotype samples. It is statistically judged that, when the genotype of the sample is double mutant GG, the caffeine content in the dry matter in the tea plant is more likely to be lower than genotype is wild type AA or single mutant GA.

The SNP site 3 is located in the tea genome Scaffold720:596655, this site is T or C, and genotype thereof is extremely significantly correlated with the caffeine content in the dry matter of the tea plant. It is shown by correlation analysis and significance analysis verification that the caffeine content in the dry matter of the tea plant corresponding to a CC genotype sample has extremely significant difference compared with a CT genotype sample. It is statistically judged that, when the genotype of the sample is single mutant CT, the caffeine content in the dry matter in the tea plant is more likely to be lower than the normal average of the CC type.

The SNP site 4 is located in the tea genome Scaffold3614:66549, this site is C or T, and genotype thereof is extremely significantly correlated with the caffeine content in the dry matter of the tea plant. It is shown by correlation analysis and significance analysis verification that the caffeine content in the dry matter of tea soup corresponding to a CC genotype sample has extremely significant difference compared with TT and CT genotype samples. It is statistically judged that, when the genotype is double mutant CC, the caffeine content in the dry matter in the tea plant is more likely to be lower than the normal average of the sample of which the genotype is wild type TT or single mutant CT.

The SNP site 5 is located in the tea genome Scaffold349:3413816, this site is G or A, and genotype thereof is extremely significantly correlated with the caffeine content in the dry matter of the tea plant. It is shown by correlation analysis and significance analysis verification that the caffeine content in the dry matter of tea soup corresponding to a GG genotype sample has extremely significant difference compared with GA and AA genotype samples. It is statistically judged that, when the genotype is double mutant GG, the caffeine content in the dry matter in the tea plant is more likely to be lower than the normal average of the sample of which the genotype is wild type AA or single mutant GA.

The SNP site 6 is located in the tea genome Scaffold920:281727, this site is G or A, and genotype thereof is extremely significantly correlated with the caffeine content in the dry matter of the tea plant. It is shown by correlation analysis and significance analysis verification that the caffeine content in the dry matter of tea soup corresponding to a GG genotype sample has extremely significant difference compared with GA and AA genotype samples. It is statistically judged that, when the genotype is double mutant GG, the caffeine content in the dry matter in the tea plant is more likely to be lower than the normal average of the sample of which the genotype is wild type AA or single mutant GA.

It is further established a detection method for detecting the six SNP sites, which can be used to evaluate the caffeine content of the tea plant, for further use in screening of tea plant resources and molecular breeding. This is the basis for molecular marker-assisted selective breeding for tea plant, which has great research value.

BRIEF DESCRIPTION OF THE DRAWINGS

FIG. 2 shows a schematic diagram of a site Scaffold4239:309117 (as shown in SEQ ID NO: 1) and primers, wherein N denotes a base to be tested at Scaffold4239:309117, and bold and underlined parts denote upstream and downstream primers (upstream primer as shown in SEQ ID NO: 2, downstream primer: CCGCAAGAGACTGTAAGTGT (SEQ ID NO: 19)).

FIG. 3 shows a schematic diagram of a site Scaffold115:803980 (as shown in SEQ ID NO: 4) and primers, wherein N denotes a base to be tested at Scaffold115:803980, and bold and underlined parts denote upstream and downstream primers (upstream primer as shown in SEQ ID NO: 5, downstream primer: CTCTCTTTGCTACTTTGGGC (SEQ ID NO: 20)).

FIG. 4 shows a schematic diagram of a site Scaffold720: 596655 (as shown in SEQ ID NO: 7) and primers, wherein N denotes a base to be tested at Scaffold720:596655, and bold and underlined parts denote upstream and downstream primers (upstream primer as shown in SEQ ID NO: 8, downstream primer: GCGTCTACACACCAGTTGAA (SEQ ID NO: 21)).

FIG. 5 shows a schematic diagram of a site Scaffold3614: 66549 (as shown in SEQ ID NO: 10) and primers, wherein N denotes a base to be tested at Scaffold3614:66549, and bold and underlined parts denote upstream and downstream primers (upstream primer as shown in SEQ ID NO: 11, downstream primer: GTCCTTACCGGGCATACATT (SEQ ID NO: 22)).

FIG. 6 shows a schematic diagram of a site Scaffold349: 3413816 (as shown in SEQ ID NO: 13) and primers, wherein N denotes a base to be tested at Scaffold349: 3413816, and bold and underlined parts denote upstream and downstream primers (upstream primer as shown in SEQ ID NO: 14, downstream primer: CCTTCTAAGAAAGTGTGGTG (SEQ ID NO: 23)).

FIG. 7 shows a schematic diagram of a site Scaffold920: 281727 (as shown in SEQ ID NO: 16) and primers, wherein N denotes a base to be tested at Scaffold920:281727, and bold and underlined parts denote upstream and downstream primers (upstream primer as shown in SEQ ID NO: 17, downstream primer: GGATGGAGAATGTAGCACGT (SEQ ID NO: 24)).

DETAILED DESCRIPTION OF THE INVENTION

Figure 1:
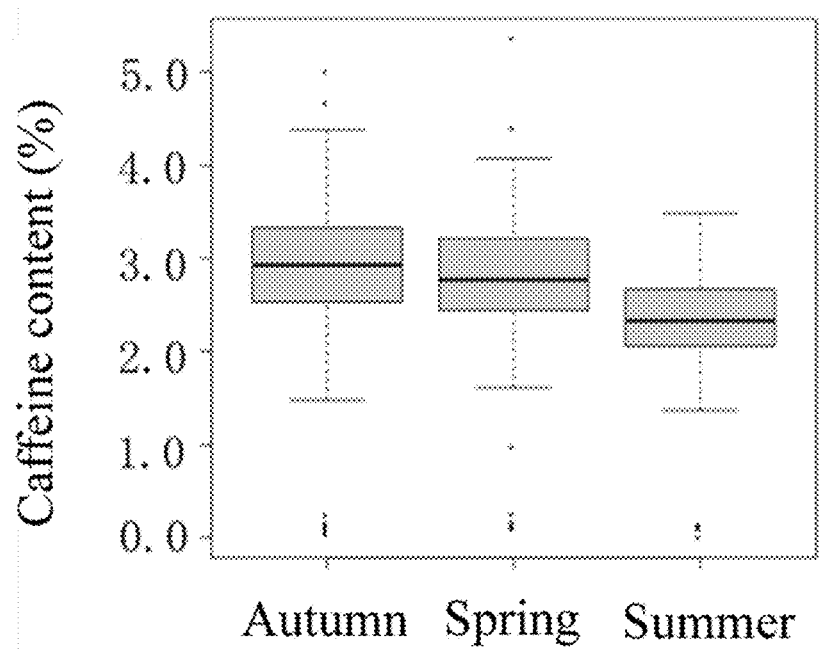
FIG. 1 shows caffeine content in different seasons.
Figure 8:
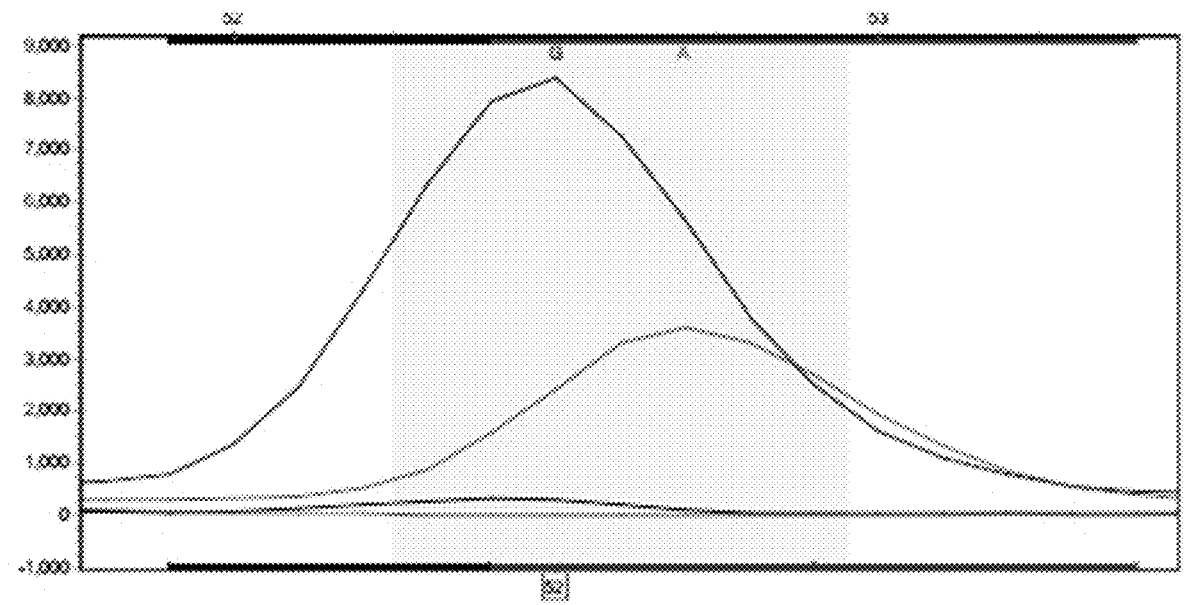
FIG. 8 shows SNaPshot sequencing results of genotype of the sample 2-72 at the site Scaffold4239:309117.
Figure 9:
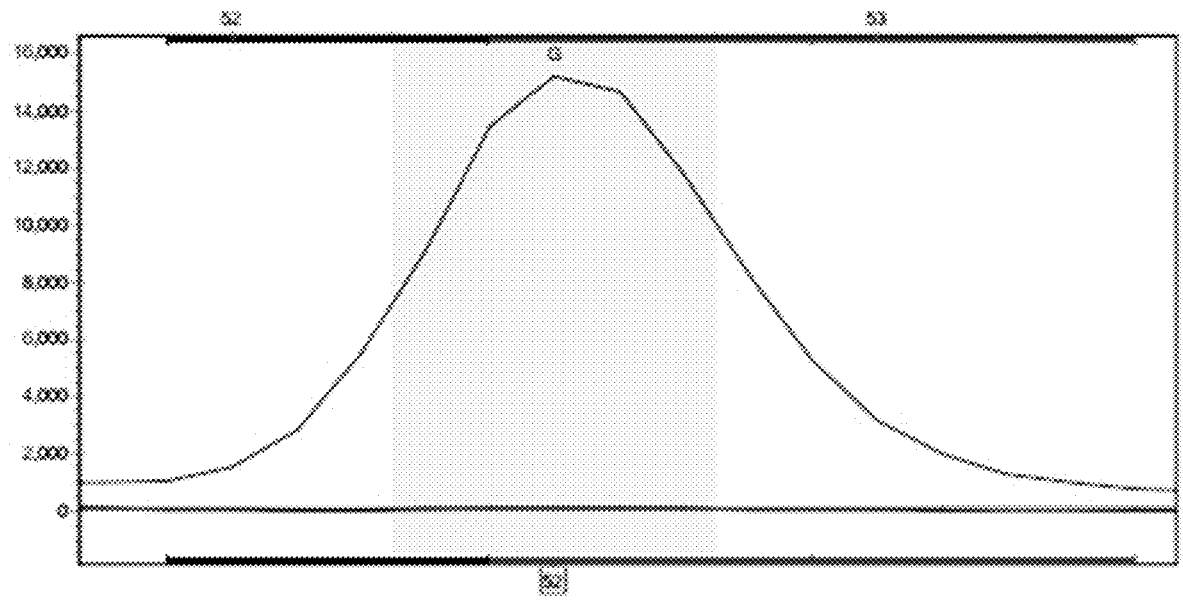
FIG. 9 shows SNaPshot sequencing results of genotype at the site Scaffold4239:309117 of the sample 2-78.
Figure 10:
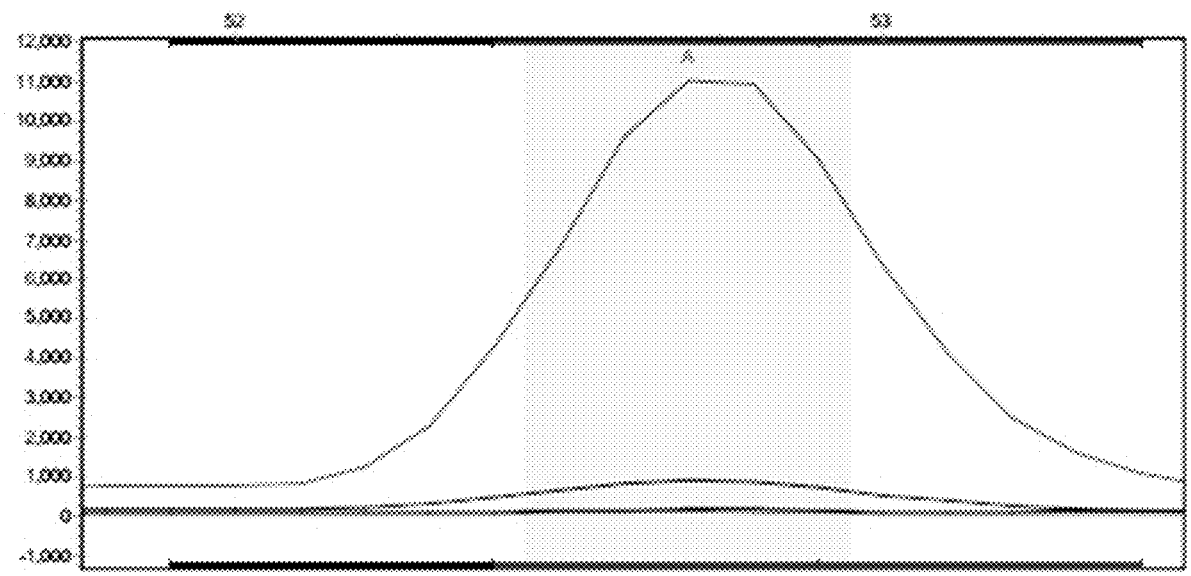
FIG. 10 shows SNaPshot sequencing results of genotype of the sample 2-97 at the site Scaffold4239:309117.
Figure 11:
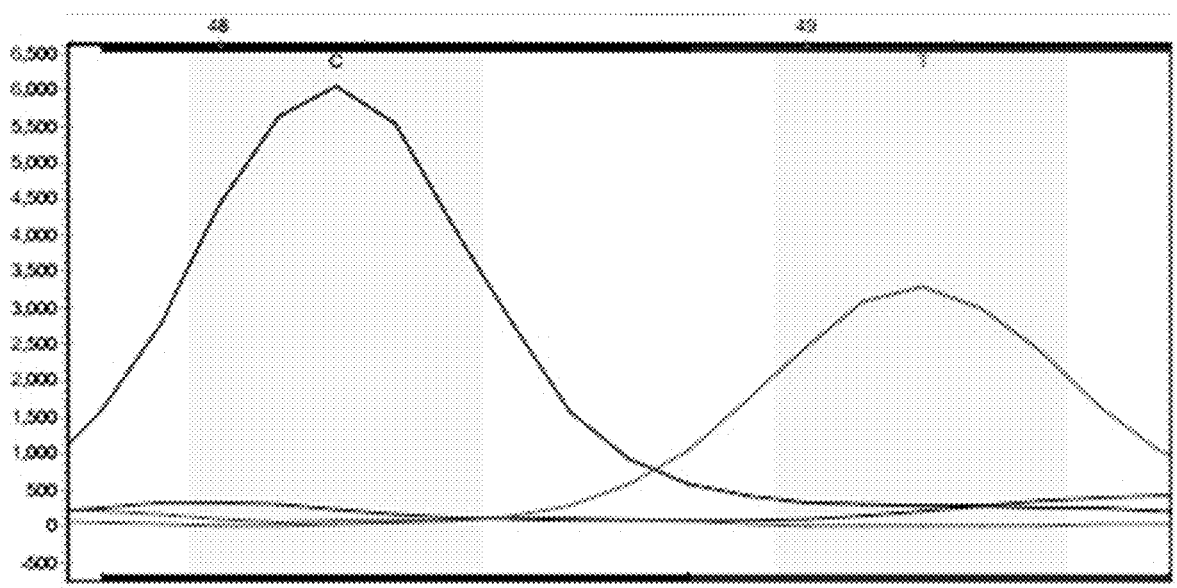
FIG. 11 shows SNaPshot sequencing results of genotype of the sample 2-77 at the site Scaffold720:596655.
Figure 12:
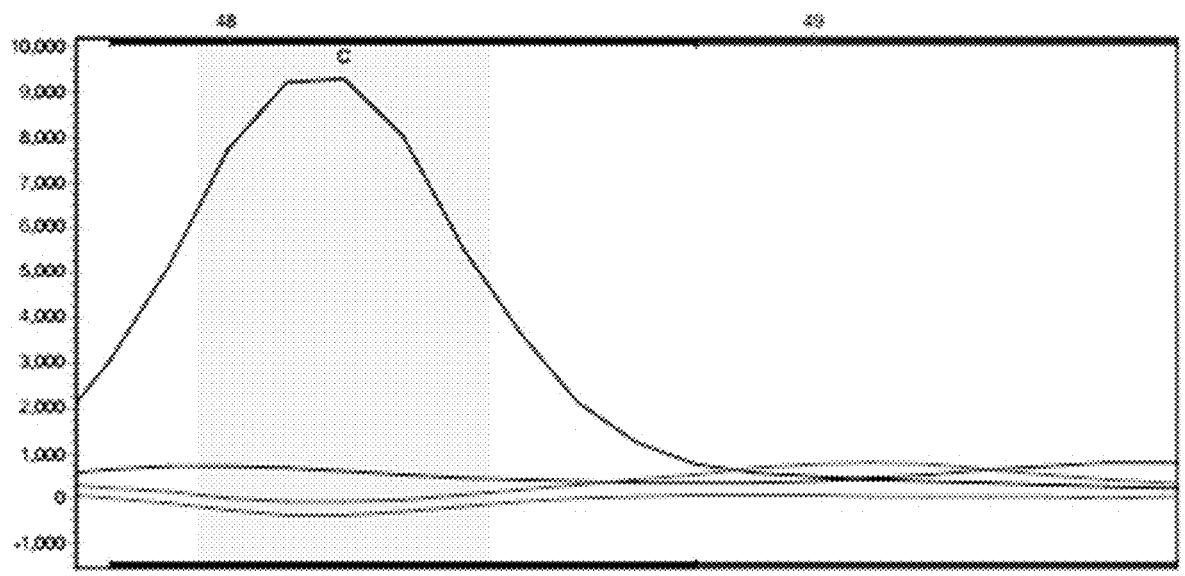
FIG. 12 shows SNaPshot sequencing results of genotype of the sample 2-81 at the site Scaffold720:596655.
Figure 13:
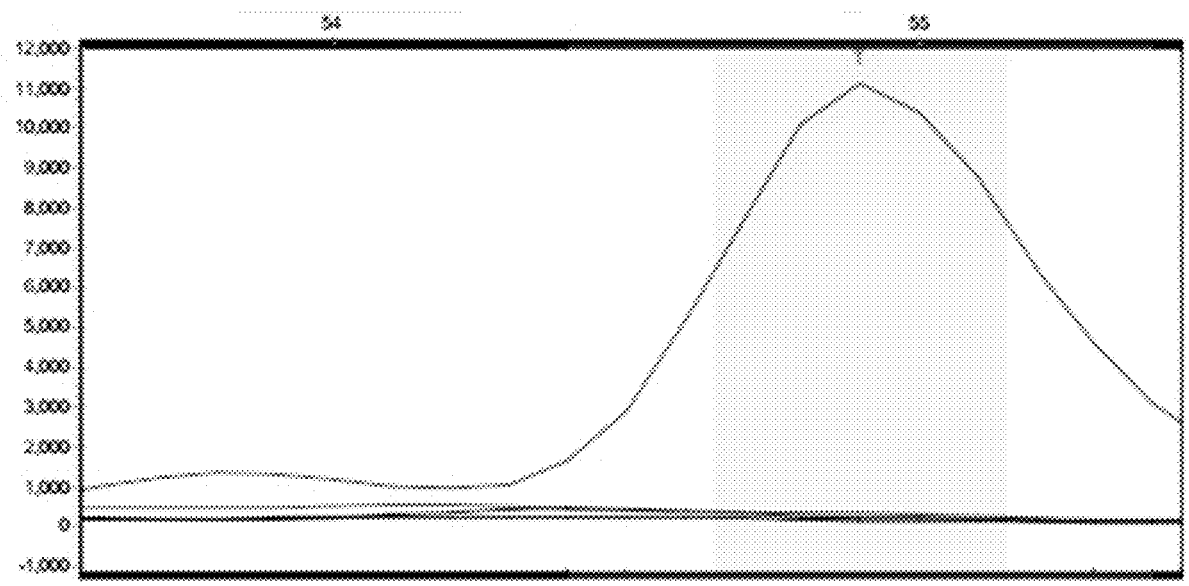
FIG. 13 shows SNaPshot sequencing results of genotype of the sample 2-23 at the site Scaffold115:803980 (reverse compliment).
Figure 14:
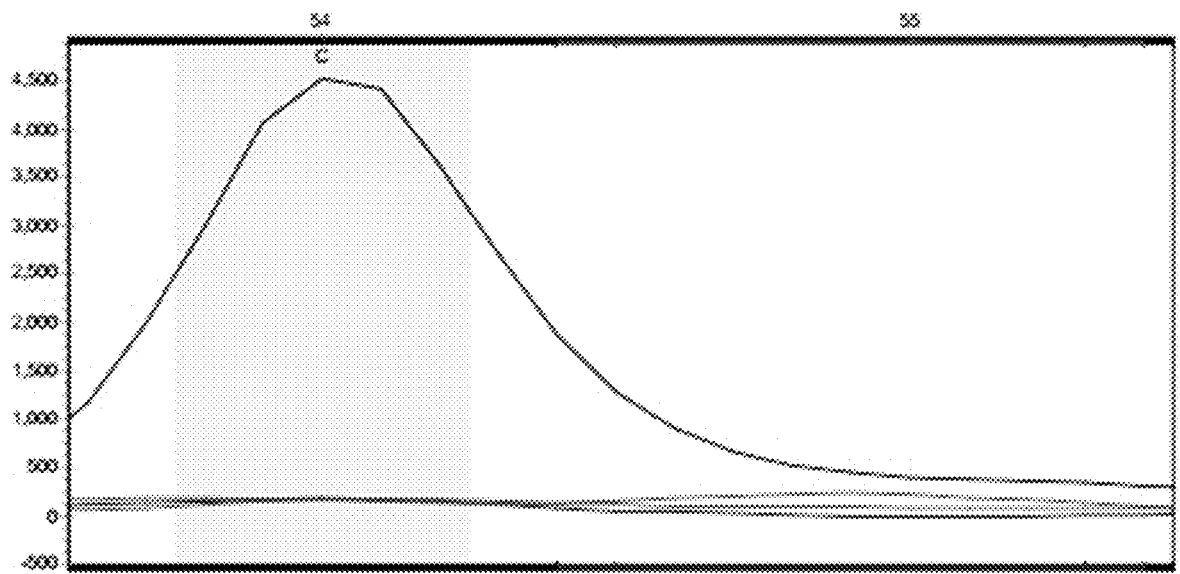
FIG. 14 shows SNaPshot sequencing results of genotype of the sample 2-97 at the site Scaffold115:803980 (reverse compliment).
Figure 15:
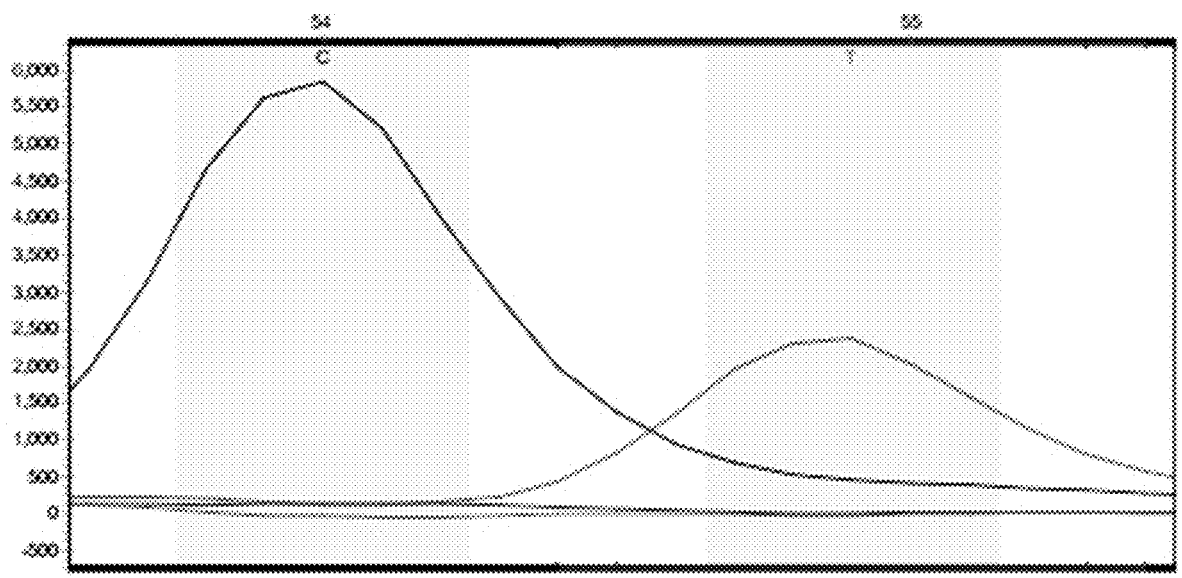
FIG. 15 shows SNaPshot sequencing results of genotype of the sample 2-80 at the site Scaffold115:803980 (reverse compliment).
Figure 16:
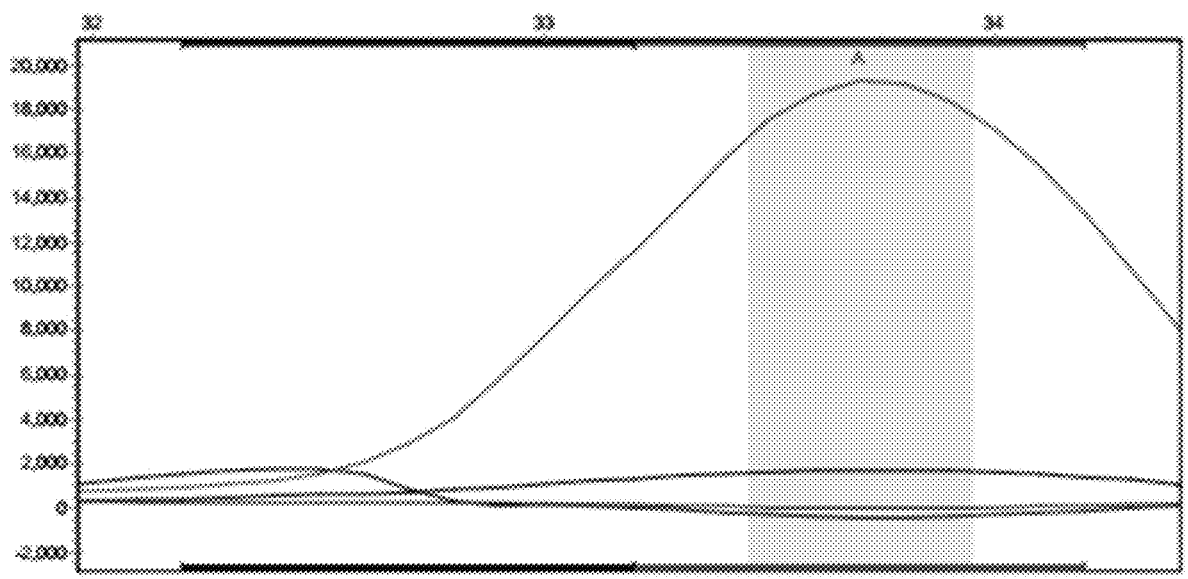
FIG. 16 shows SNaPshot sequencing results of genotype of the sample 2-70 at the site Scaffold3614:66549 (reverse compliment).
Figure 17:
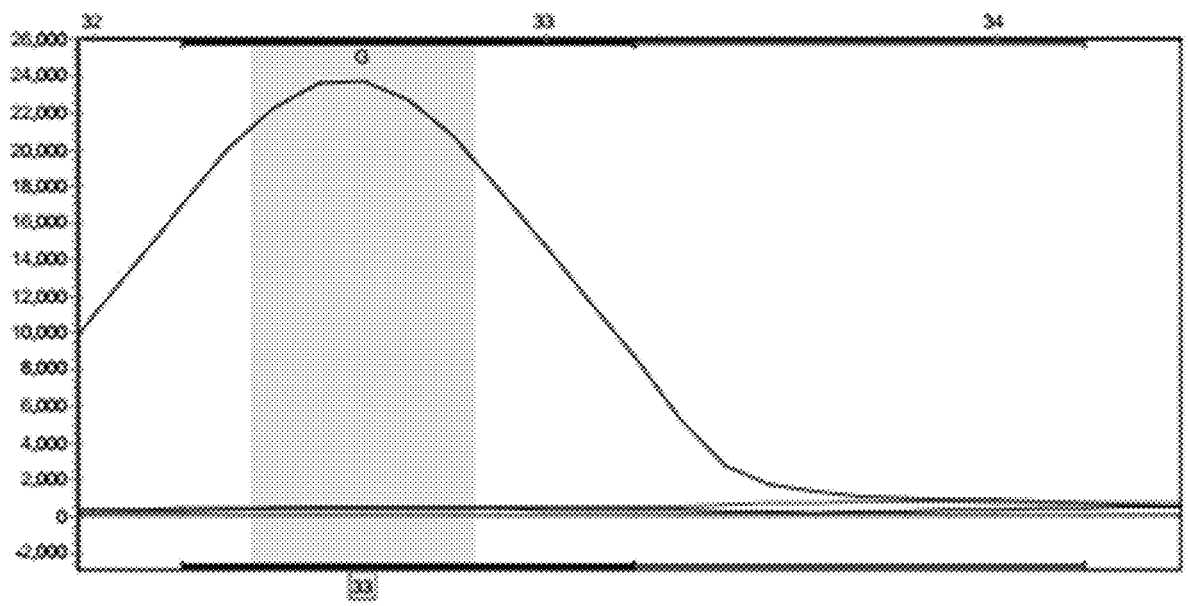
FIG. 17 shows SNaPshot sequencing results of genotype of the sample 2-77 at the site Scaffold3614:66549 (reverse compliment).
Figure 18:
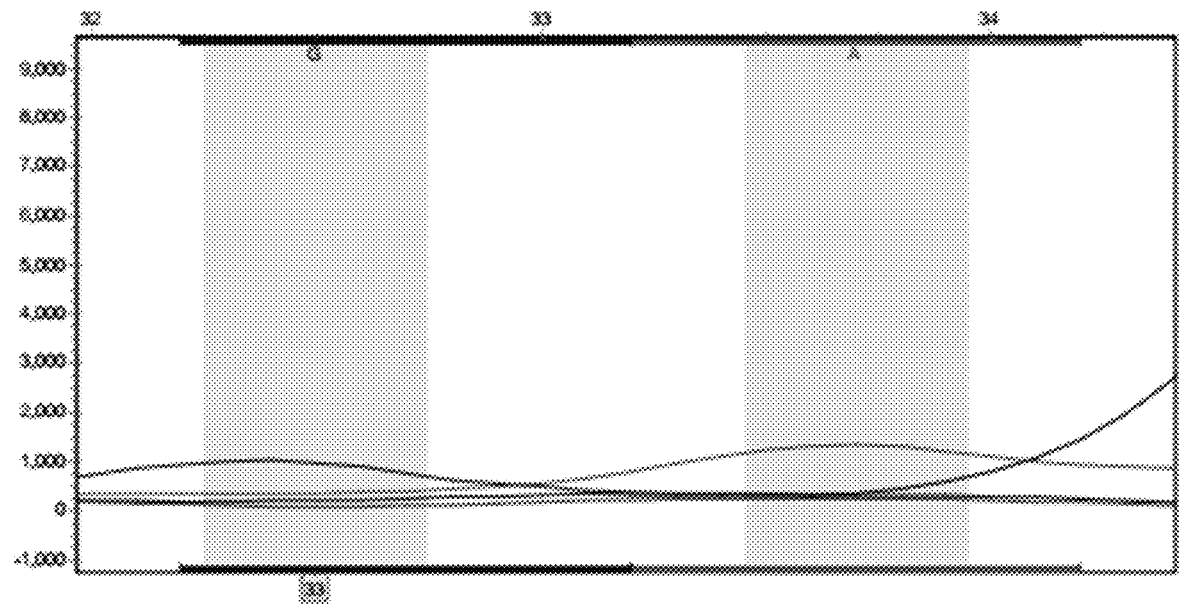
FIG. 18 shows SNaPshot sequencing results of genotype of the sample 2-72 at the site Scaffold3614:66549 (reverse compliment).
Figure 19:
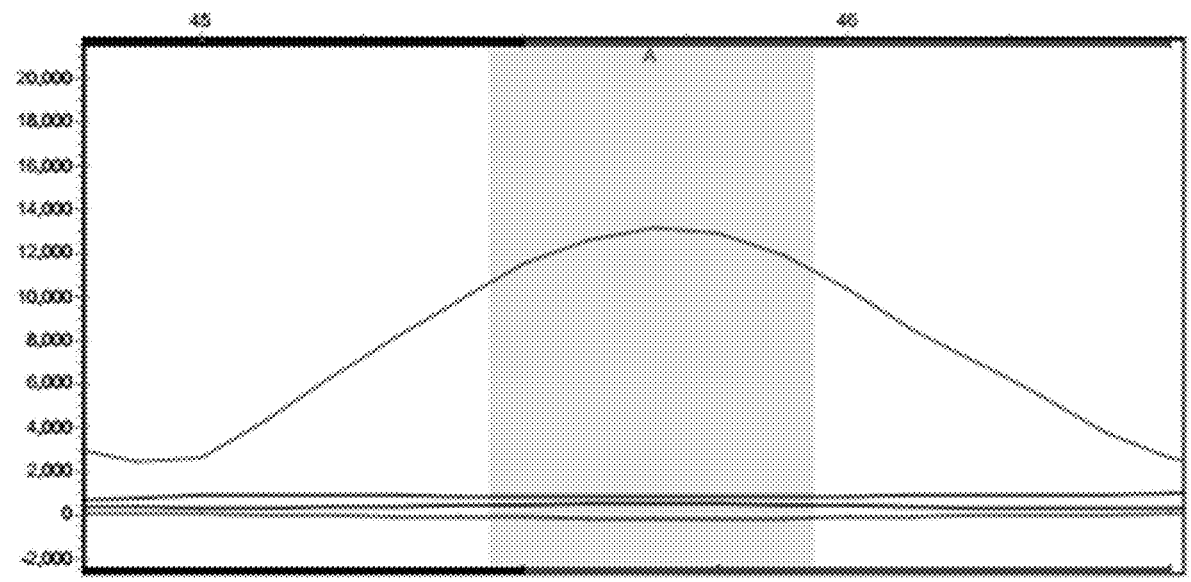
FIG. 19 shows SNaPshot sequencing results of genotype of the sample 2-69 at the site Scaffold349:3413816.
Figure 20:
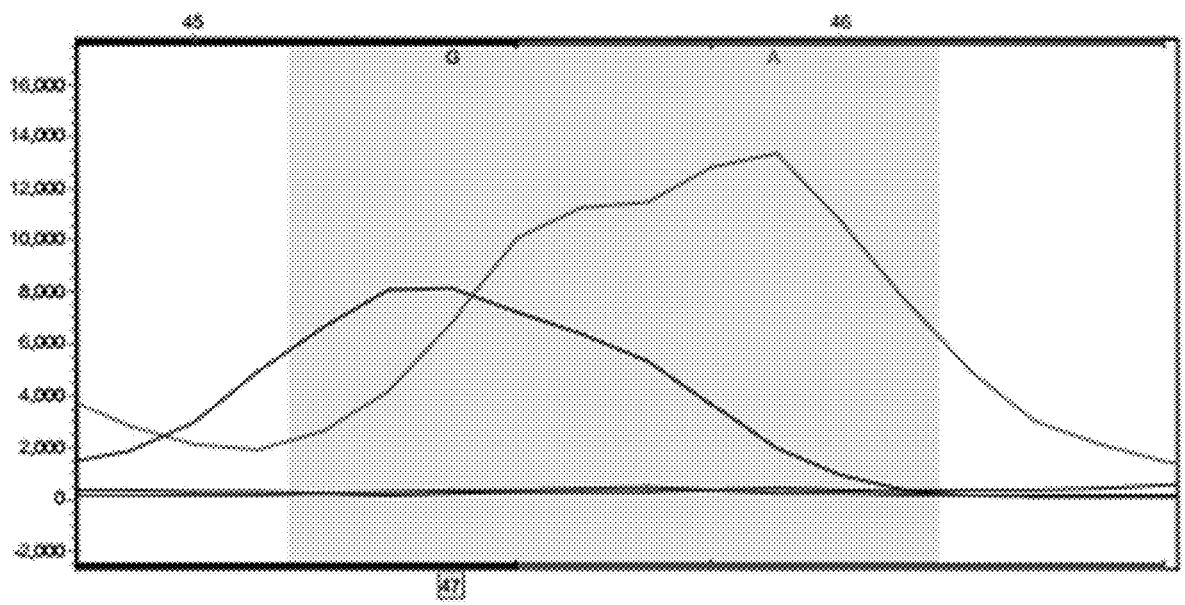
FIG. 20 shows SNaPshot sequencing results of genotype of the sample 2-68 at the site Scaffold349:3413816.
Figure 21:
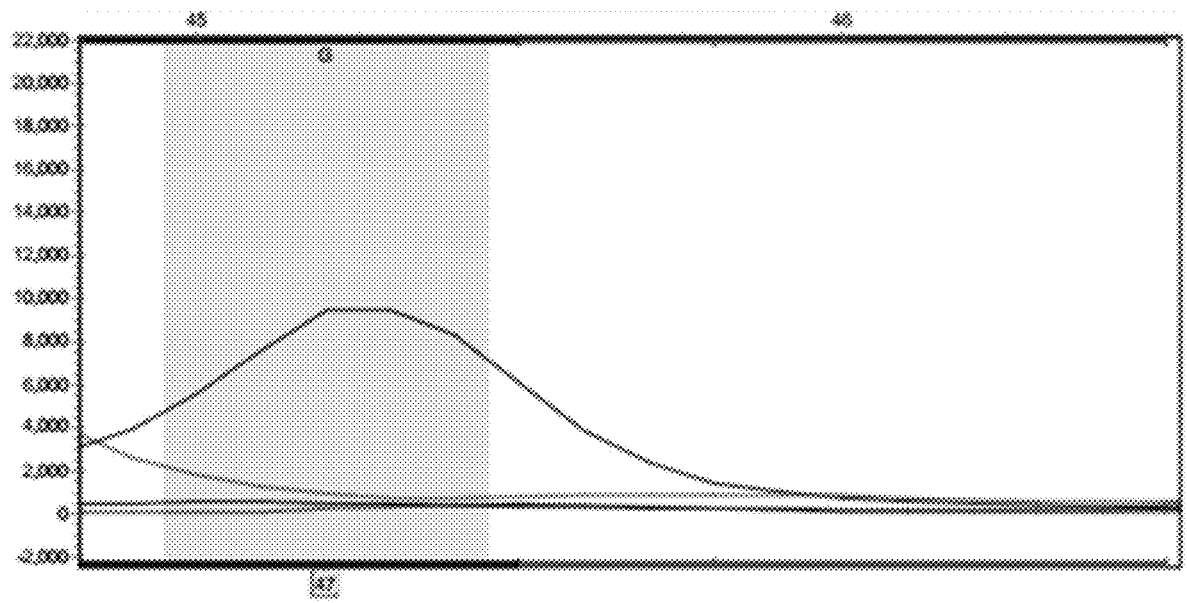
FIG. 21 shows SNaPshot sequencing results of genotype of the sample 2-77 at the site Scaffold349:3413816.
Figure 22:
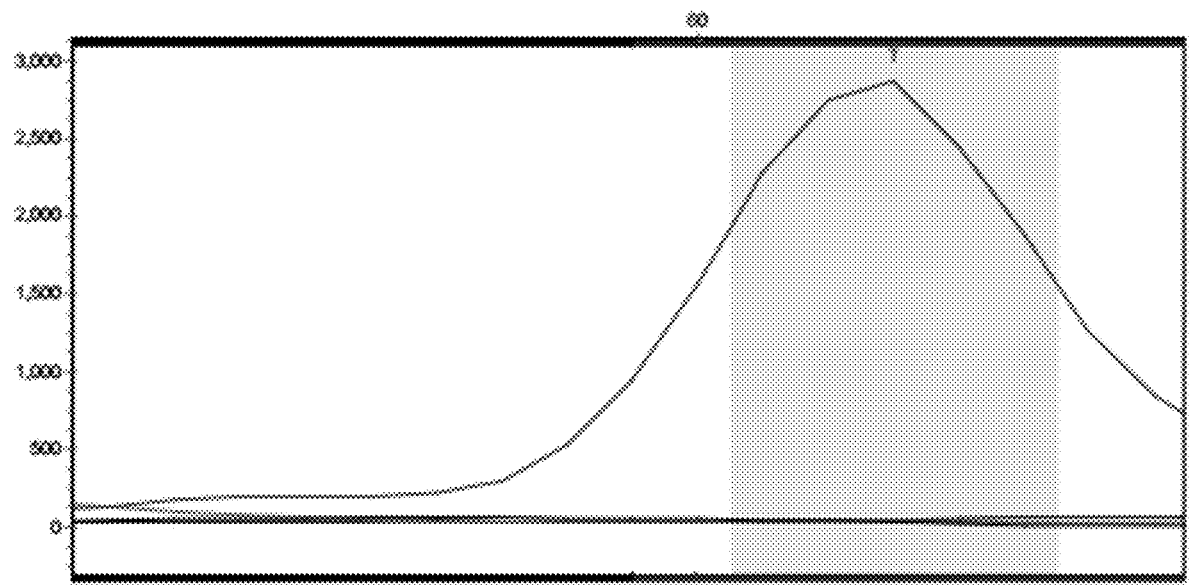
FIG. 22 shows SNaPshot sequencing results of genotype of the sample 2-72 at the site Scaffold920:281727 (reverse compliment).
Figure 23:
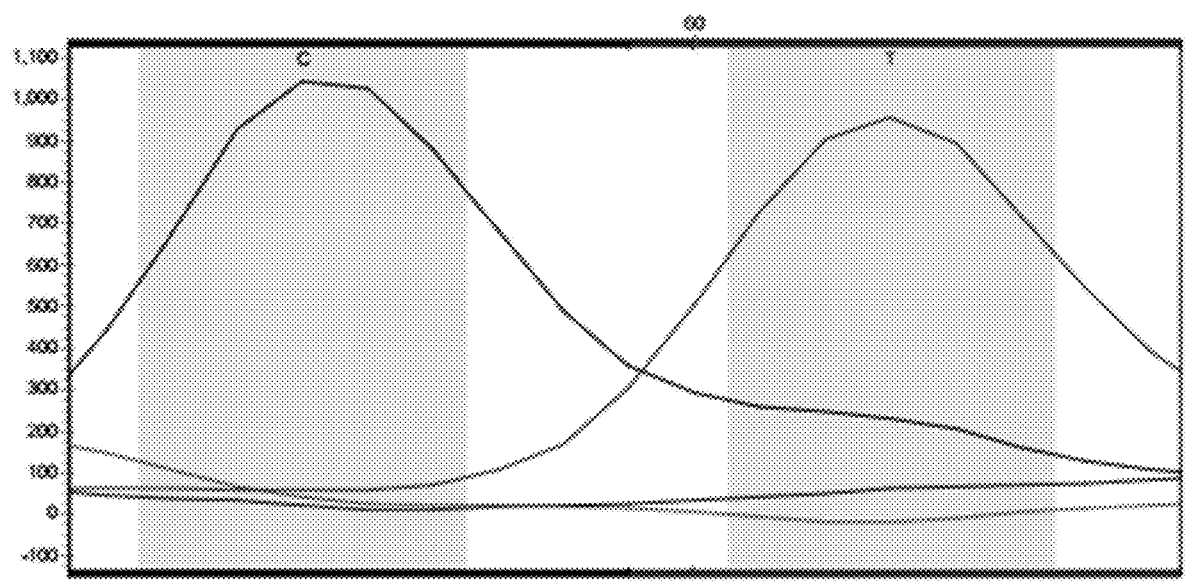
FIG. 23 shows SNaPshot sequencing results of genotype of the sample 2-94 at the site Scaffold920:281727 (reverse compliment).
Figure 24:
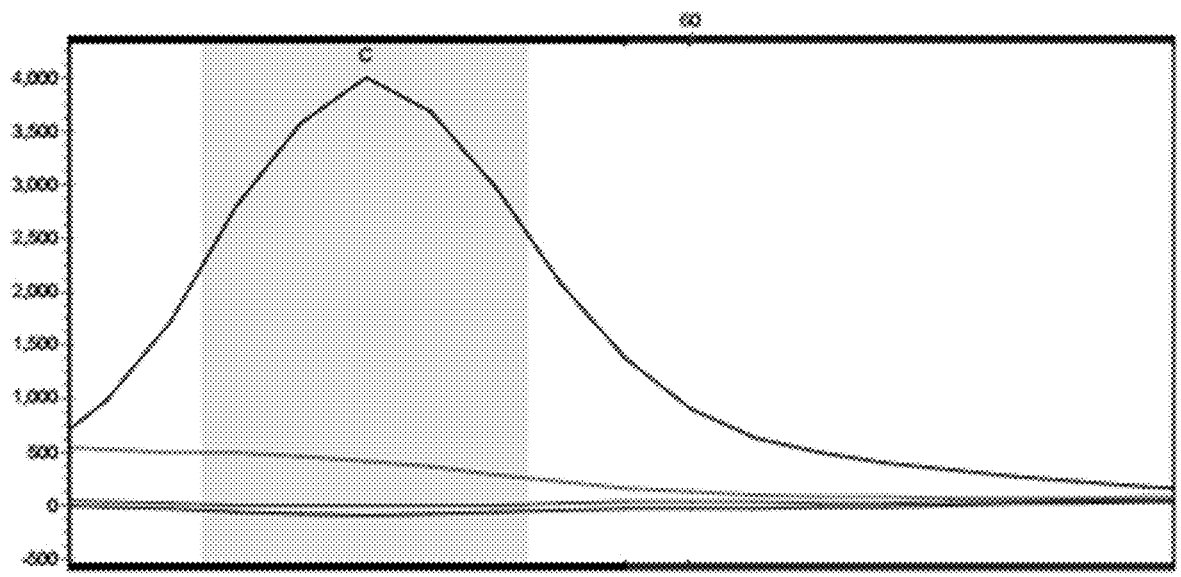
FIG. 24 shows SNaPshot sequencing results of genotype of the sample 2-97 at the site Scaffold920:281727 (reverse compliment).
Figure 25:
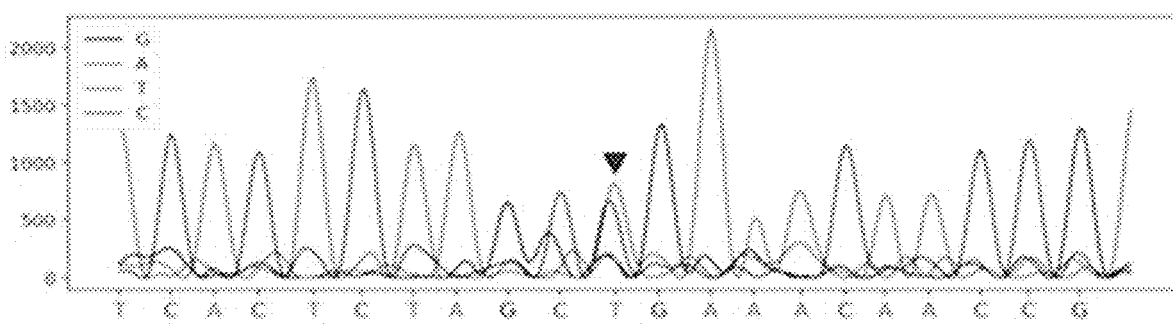
FIG. 25 shows sequencing results of genotype at the site Scaffold4239:309117.
Figure 26:
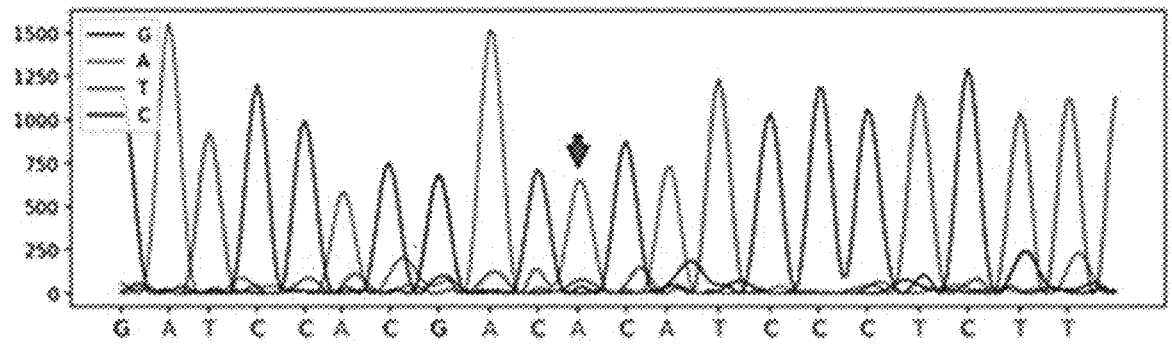
FIG. 26 shows sequencing results of genotype at the site Scaffold115:803980, AA genotype.
Figure 27:
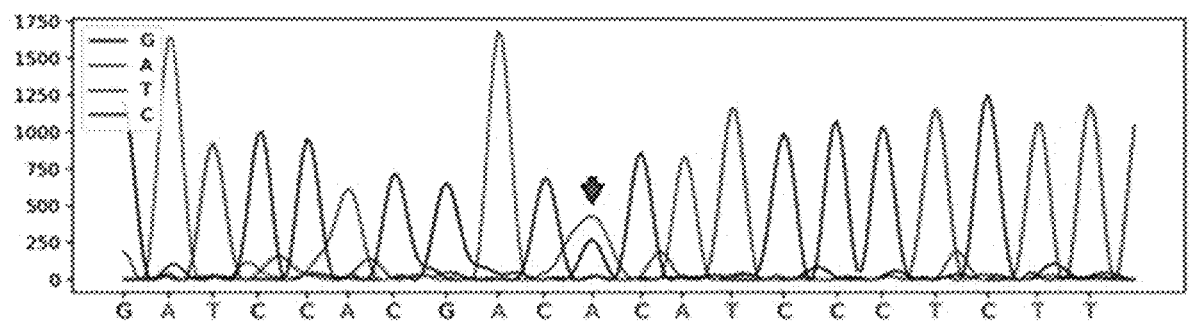
FIG. 27 shows sequencing results of genotype at the site Scaffold115:803980, GA genotype.
Figure 28:
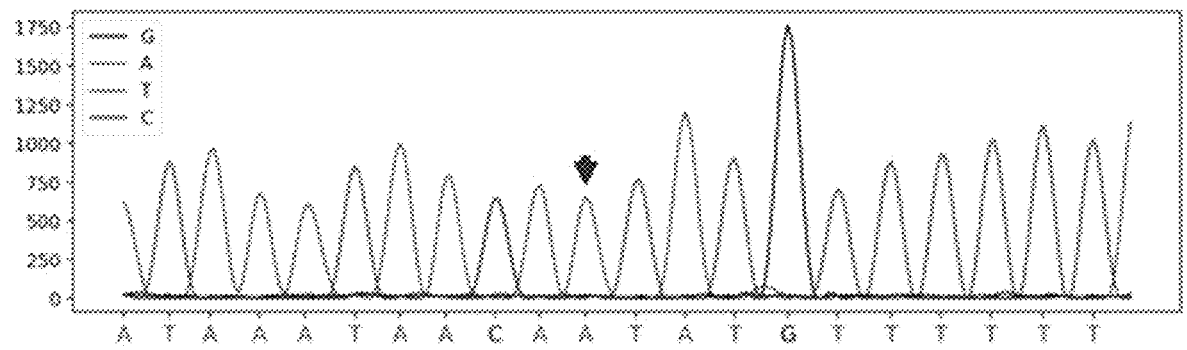
FIG. 28 shows sequencing results of genotype at the site Scaffold349:3413816.
Figure 29:
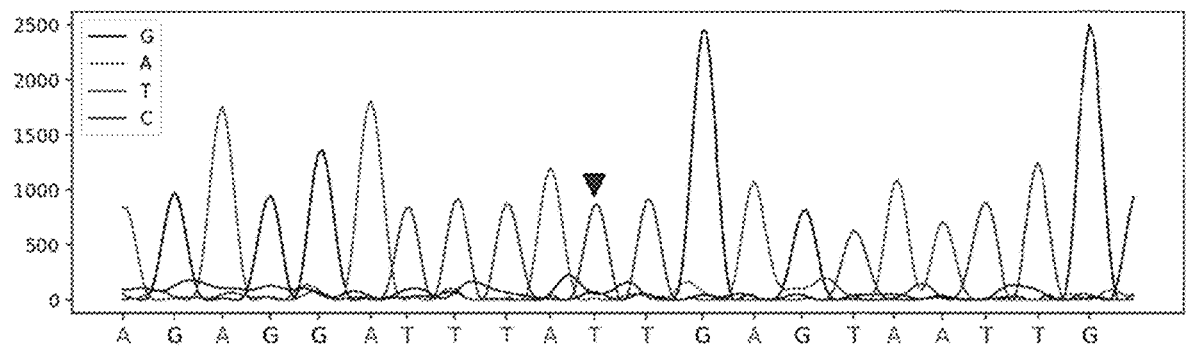
FIG. 29 shows sequencing results of genotype at the site Scaffold920:281727.

The present invention will be further described in detail below with reference to the accompanying drawings and specific embodiments, and the embodiments are only used to explain the present invention, and are not used to limit the scope of the present invention. The test methods used in the following embodiments are all conventional methods unless otherwise specified. The materials and agents used, unless otherwise specified, are the agents and materials available from commercial sources.

Embodiment 1

I. Experiment Sample 191 tea plant materials located in Guangdong Province Tea Plant Germplasm Resource Bank (Yingde, Guangdong, 113.3OE, 24.3ON) were collected, including 124 from Guangdong, 20 from Fujian, 14 from Guangxi, 9 from Zhejiang, 6 from Hunan, 6 from Yunnan, 1 from Jiangxi, 1 from Guizhou, 1 from Taiwan, and 8 offspring of Kenyan tea, 1 offspring of Georgian species. The selected materials are widely representative.

The selected resources are randomly distributed in the resource bank. Double row per plant was used, each row is 4 m, the row spacing is 1.5 m, and the plant spacing is 35 cm. The resource bank was subjected to conventional water and fertilizer management. At the end of 2016, the resources were pruned and deep pits were applied with base fertilizer, 4 tons of organic fertilizer, 0.75 tons of peanut bran and 5 kg of compound fertilizer per acre. After picking spring tea and summer tea in 2017, pruning and topdressing outside the root were conducted, 15 kg compound fertilizer and 30 kg urea per acre. On Mar. 15, 2017, Jun. 25, 2017, and Sep. 28, 2017, the new shoots (one bud with two leaves) of the tea plant were picked, to make steamed green samples, and tea soup was prepared according to water extraction method.

II. Phenotypic Data Analysis

1. Experimental Procedure

The high-performance liquid chromatography was used to detect caffeine in tea soup related to the taste of tea plant, referring to the Chinese standard detection method.

2. Experimental Results

Caffeine content is shown in Table 1.

TABLE 1

Percentage of caffeine in dry matter from different resources in different seasons:

| Sample | Caffeine content (%) | | |
|---|---|---|---|
| | Spring | Summer | Autumn |
| Sample 1 | 1.98 | 1.42 | 2.23 |
| Sample 2 | 2.88 | 2.05 | 2.64 |
| Sample 3 | 2.16 | 2.31 | 2.16 |
| Sample 4 | 2.49 | 2.28 | 3.07 |
| Sample 5 | 2.49 | 2.24 | 2.90 |
| Sample 6 | 1.98 | 1.75 | 2.58 |
| Sample 7 | 1.73 | 2.01 | 2.58 |
| Sample 8 | 2.00 | 2.36 | 3.12 |
| Sample 9 | 3.75 | 2.35 | 3.42 |
| Sample 10 | 2.49 | 2.36 | 2.82 |
| Sample 11 | 3.17 | 2.66 | 3.31 |
| Sample 12 | 1.85 | 3.12 | 2.56 |
| Sample 13 | 2.46 | 2.53 | 2.60 |
| Sample 14 | 1.61 | 2.54 | 3.72 |
| Sample 15 | 3.94 | 2.36 | 2.15 |
| Sample 16 | 3.27 | 2.75 | 3.30 |
| Sample 17 | 2.52 | 1.79 | 2.59 |
| Sample 18 | 2.80 | 1.92 | 3.02 |
| Sample 19 | 3.40 | 1.98 | 2.93 |
| Sample 20 | 2.81 | 2.04 | 2.22 |
| Sample 21 | 2.14 | 1.86 | 1.98 |
| Sample 22 | 3.39 | 2.67 | 3.12 |
| Sample 23 | 4.39 | 2.70 | 1.91 |
| Sample 24 | 2.70 | 2.76 | 2.55 |
| Sample 25 | 3.06 | 2.40 | 1.91 |
| Sample 26 | 2.48 | 3.41 | 2.98 |
| Sample 27 | 2.29 | 1.56 | 2.77 |
| Sample 28 | 2.47 | 2.16 | 2.46 |
| Sample 29 | 0.09 | 0.09 | 0.11 |
| Sample 30 | 2.63 | 2.69 | 3.19 |
| Sample 31 | 2.77 | 1.79 | 3.27 |
| Sample 32 | 2.67 | 2.31 | 3.36 |
| Sample 33 | 2.24 | 3.36 | 2.52 |
| Sample 34 | 2.51 | 2.43 | 2.62 |
| Sample 35 | 2.27 | 2.34 | 2.47 |
| Sample 36 | 2.73 | 2.98 | 2.82 |
| Sample 37 | 1.91 | 2.45 | 3.37 |
| Sample 38 | 2.74 | 1.81 | 3.02 |
| Sample 39 | 3.54 | 2.20 | 3.15 |
| Sample 40 | 2.43 | 2.55 | 2.46 |
| Sample 41 | 3.10 | 2.28 | 2.46 |
| Sample 42 | 2.44 | 1.84 | 2.69 |
| Sample 43 | 3.07 | 2.62 | 3.21 |
| Sample 44 | 2.13 | 2.67 | 2.95 |
| Sample 45 | 2.79 | 2.76 | 2.88 |
| Sample 46 | 2.95 | 2.23 | 3.48 |
| Sample 47 | 2.66 | 1.44 | 2.50 |
| Sample 48 | 2.46 | 2.29 | 2.53 |
| Sample 49 | 2.74 | 2.54 | 3.29 |
| Sample 50 | 2.30 | 2.25 | 2.41 |
| Sample 51 | 2.51 | 2.68 | 3.51 |
| Sample 52 | 2.55 | 2.36 | 1.91 |
| Sample 53 | 2.91 | 2.89 | 3.15 |
| Sample 54 | 2.17 | 2.53 | 2.87 |
| Sample 55 | 3.34 | 2.30 | 2.81 |
| Sample 56 | 2.44 | 2.24 | 3.14 |
| Sample 57 | 3.14 | 3.18 | 3.08 |
| Sample 58 | 2.69 | 2.28 | 3.56 |
| Sample 59 | 2.25 | 2.16 | 2.23 |
| Sample 60 | 2.24 | 2.52 | 2.95 |
| Sample 61 | 2.16 | 2.36 | 2.05 |
| Sample 62 | 2.59 | 2.89 | 3.61 |
| Sample 63 | 2.66 | 2.06 | 3.39 |
| Sample 64 | 2.36 | 2.60 | 3.48 |
| Sample 65 | 2.44 | 3.32 | 3.06 |
| Sample 66 | 3.39 | 2.71 | 2.85 |
| Sample 67 | 2.84 | 1.82 | 4.15 |
| Sample 68 | 2.63 | 2.05 | 2.70 |
| Sample 69 | 3.04 | 2.52 | 2.99 |
| Sample 70 | 2.73 | 2.89 | 2.90 |
| Sample 71 | 3.23 | 2.42 | 3.41 |
| Sample 72 | 3.04 | 2.65 | 3.44 |
| Sample 73 | 2.74 | 1.90 | 3.00 |
| Sample 74 | 2.79 | 2.68 | 3.00 |
| Sample 75 | 2.86 | 1.85 | 3.05 |
| Sample 76 | 3.16 | 2.75 | 3.52 |
| Sample 77 | 3.09 | 2.33 | 2.58 |
| Sample 78 | 0.13 | 0.11 | 0.04 |
| Sample 79 | 0.10 | 0.00 | 0.03 |
| Sample 80 | 3.14 | 1.81 | 3.05 |
| Sample 81 | 0.10 | 0.09 | 0.10 |
| Sample 82 | 2.07 | 2.67 | 3.61 |
| Sample 83 | 3.17 | 2.88 | 3.64 |
| Sample 84 | 2.38 | 1.72 | 2.93 |
| Sample 85 | 2.68 | 2.62 | 2.25 |
| Sample 86 | 2.78 | 3.27 | 3.29 |
| Sample 87 | 2.22 | 2.29 | 2.85 |
| Sample 88 | 2.70 | 1.56 | 2.77 |
| Sample 89 | 2.32 | 2.21 | 2.53 |
| Sample 90 | 2.08 | 1.89 | 2.31 |
| Sample 91 | 2.29 | 2.72 | 2.50 |
| Sample 92 | 2.68 | 2.70 | 2.73 |
| Sample 93 | 2.26 | 3.19 | 2.74 |
| Sample 94 | 2.88 | 2.71 | 2.61 |
| Sample 95 | 2.73 | 2.36 | 2.99 |
| Sample 96 | 2.46 | 1.83 | 2.46 |
| Sample 97 | 1.67 | 2.81 | 2.29 |
| Sample 98 | 2.64 | 3.20 | 4.00 |
| Sample 99 | 3.18 | 2.24 | 2.68 |
| Sample 100 | 2.48 | 2.05 | 2.00 |
| Sample 101 | 2.19 | 1.92 | 3.37 |
| Sample 102 | 2.49 | 1.98 | 2.90 |
| Sample 103 | 2.94 | 2.58 | 2.82 |
| Sample 104 | 2.47 | 2.58 | 3.33 |
| Sample 105 | 3.90 | 2.38 | 3.43 |
| Sample 106 | 2.41 | 2.02 | 2.93 |
| Sample 107 | 3.32 | 2.80 | 3.61 |
| Sample 108 | 1.61 | 2.07 | 2.40 |
| Sample 109 | 3.04 | 2.47 | 2.92 |
| Sample 110 | 3.00 | 2.28 | 3.74 |
| Sample 111 | 3.98 | 3.25 | 2.77 |
| Sample 112 | 3.88 | 2.65 | 3.08 |
| Sample 113 | 3.36 | 1.97 | 3.01 |
| Sample 114 | 3.82 | 3.04 | 3.68 |
| Sample 115 | 4.07 | 3.30 | 3.88 |
| Sample 116 | 2.51 | 2.21 | 2.72 |
| Sample 117 | 2.98 | 2.85 | 3.47 |
| Sample 118 | 3.34 | 2.32 | 3.11 |
| Sample 119 | 2.93 | 2.62 | 2.87 |
| Sample 120 | 3.25 | 2.49 | 3.40 |
| Sample 121 | 2.87 | 2.21 | 2.99 |
| Sample 122 | 3.03 | 2.27 | 1.90 |
| Sample 123 | 3.08 | 2.43 | 3.28 |
| Sample 124 | 3.25 | 2.71 | 2.95 |
| Sample 125 | 2.58 | 2.90 | 3.46 |
| Sample 126 | 3.30 | 2.38 | 4.26 |
| Sample 127 | 3.02 | 2.26 | 2.83 |
| Sample 128 | 0.97 | 2.58 | 3.61 |
| Sample 129 | 1.67 | 1.77 | 2.34 |
| Sample 130 | 3.31 | 2.08 | 2.83 |
| Sample 131 | 3.58 | 2.38 | 3.08 |
| Sample 132 | 3.45 | 1.99 | 2.50 |
| Sample 133 | 3.58 | 2.16 | 3.75 |
| Sample 134 | 2.69 | 2.47 | 2.55 |
| Sample 135 | 2.80 | 1.72 | 2.42 |
| Sample 136 | 3.84 | 2.06 | 2.12 |
| Sample 137 | 0.25 | 0.11 | 0.08 |
| Sample 138 | 2.42 | 2.01 | 2.54 |
| Sample 139 | 0.11 | 0.13 | 0.13 |
| Sample 140 | 2.97 | 2.11 | 2.90 |
| Sample 141 | 2.92 | 2.31 | 2.62 |
| Sample 142 | 2.84 | 2.72 | 2.82 |

TABLE 1-continued

Percentage of caffeine in dry matter from different resources in different seasons:

| Sample | Caffeine content (%) | | |
|---|---|---|---|
| | Spring | Summer | Autumn |
| Sample 143 | 2.75 | 2.83 | 3.63 |
| Sample 144 | 2.74 | 2.31 | 3.02 |
| Sample 145 | 3.22 | 2.71 | 3.27 |
| Sample 146 | 2.83 | 2.20 | 1.91 |
| Sample 147 | 3.01 | 2.36 | 3.54 |
| Sample 148 | 3.61 | 2.13 | 2.30 |
| Sample 149 | 2.45 | 1.93 | 0.14 |
| Sample 150 | 2.97 | 2.18 | 5.00 |
| Sample 151 | 3.70 | 3.00 | 3.03 |
| Sample 152 | 3.08 | 2.47 | 2.72 |
| Sample 153 | 3.32 | 2.88 | 2.85 |
| Sample 154 | 1.98 | 1.86 | 3.52 |
| Sample 155 | 2.48 | 2.20 | 2.44 |
| Sample 156 | 3.96 | 3.13 | 3.84 |
| Sample 157 | 3.92 | 2.95 | 4.66 |
| Sample 158 | 3.44 | 2.24 | 2.81 |
| Sample 159 | 2.48 | 2.50 | 2.90 |
| Sample 160 | 2.55 | 2.16 | 3.18 |
| Sample 161 | 3.41 | 2.31 | 3.48 |
| Sample 162 | 3.34 | 2.08 | 3.33 |
| Sample 163 | 3.45 | 2.46 | 3.02 |
| Sample 164 | 2.90 | 2.37 | 3.00 |
| Sample 165 | 4.03 | 2.32 | 3.87 |
| Sample 166 | 3.04 | 3.10 | 3.90 |
| Sample 167 | 3.31 | 2.23 | 2.60 |
| Sample 168 | 2.22 | 3.00 | 3.53 |
| Sample 169 | 3.20 | 1.97 | 2.21 |
| Sample 170 | 3.17 | 2.44 | 3.60 |
| Sample 171 | 2.77 | 2.87 | 4.20 |
| Sample 172 | 2.23 | 2.21 | 2.98 |
| Sample 173 | 3.55 | 3.05 | 3.65 |
| Sample 174 | 2.60 | 1.77 | 2.16 |
| Sample 175 | 3.21 | 2.25 | 2.98 |
| Sample 176 | 2.74 | 1.81 | 0.24 |
| Sample 177 | 2.37 | 2.17 | 3.21 |
| Sample 178 | 3.29 | 3.48 | 4.38 |
| Sample 179 | 0.10 | 0.09 | 3.00 |
| Sample 180 | 2.95 | 1.37 | 2.71 |
| Sample 181 | 3.72 | 2.67 | 3.59 |
| Sample 182 | 3.81 | 2.69 | 3.00 |
| Sample 183 | 3.70 | 2.14 | 3.58 |
| Sample 184 | 2.82 | 1.94 | 1.48 |
| Sample 185 | 3.29 | 2.10 | 3.45 |
| Sample 186 | 3.55 | 2.23 | 2.28 |
| Sample 187 | 3.29 | 2.38 | 2.71 |
| Sample 188 | 0.16 | 0.10 | 2.44 |
| Sample 189 | 5.36 | 2.42 | 3.45 |
| Sample 190 | 3.21 | 2.63 | 2.38 |
| Sample 191 | 2.64 | 2.64 | 2.85 |

The variation of caffeine content in the population is shown in Table 2 and FIG. 1.

TABLE 2

Phenotypic variation in caffeine content:

| Season | Range (%) | Mean (%) | Standard deviation $^a$SD | Coefficient of variation $^b$CV | Diversity index $^c$H' | Heritability |
|---|---|---|---|---|---|---|
| Spring | 0.09~5.36 | 2.72 | 0.81 | 0.30 | 1.90 | 0.70 |
| Summer | 0~3.48 | 2.29 | 0.64 | 0.28 | 1.85 | |
| Autumn | 0.03~5.0 | 2.84 | 0.81 | 0.29 | 1.83 | |

III. Association Analysis between Genotype and Traits
1. Experimental Procedure

The CTAB method was used to extract total DNA from buds of 191 tea plant resources, and it was ensured that A260/A280 of each DNA sample is between 1.8 and 2.0, and the concentration was greater than 100 μg/μl. The extracted DNA samples were used to detect genotypes located in the SNP site 1 (Scaffold4239:309117), the SNP site 2 (Scaffold115:803980), the SNP site 3 (Scaffold720:596655), the SNP site 4 (Scaffold3614:66549), the SNP site 5 (Scaffold349:3413816), and the SNP site 6 (Scaffold920:281727) of the "Shuchazao" CSS cultivar tea plant genome (http://tpia.teaplant.org/index.html), respectively. The association analysis of traits and markers was performed, significance level of the association was judged by p-value, and the p-value less than 1.25E-05 was the significance level.

2. Experimental Results

The p-values of the six SNP sites in different seasons are shown in Table 3.

TABLE 3 p-values of six SNP sites in different seasons

| Season | Spring | Summer | Autumn |
|---|---|---|---|
| Scaffold4239:309117 | 6.91E-10 | 7.33E-09 | 3.28E-05 |
| Scaffold115:803980 | 6.07E-09 | 1.17E-13 | 9.38E-11 |
| Scaffold720:596655 | 1.60E-15 | 4.41E-16 | 2.56E-13 |
| Scaffold3614:66549 | 1.03E-11 | 3.15E-10 | 2.42E-08 |
| Scaffold349:3413816 | 5.68E-09 | 3.51E-10 | 7.98E-09 |
| Scaffold920:281727 | 6.12E-13 | 9.58E-12 | 4.13E-07 |

Embodiment 2 Verification of SNP Site

I. Experimental Method

Genotypes of the SNP site 1 (Scaffold4239:309117), the SNP site 2 (Scaffold115:803980), the SNP site 3 (Scaffold720:596655), the SNP site 4 (Scaffold3614:66549), the SNP site 5 (Scaffold349:3413816), and the SNP site 6 (Scaffold920:281727) were subjected to verification in another population of 98 germplasms.

1. Caffeine content of each sample was detected. The specific detection method is the same as that of Embodiment 1.
2. SnapShot technology platform was used to detect the genotypes of the SNP site 1 (Scaffold4239:309117), the SNP site 2 (Scaffold115:803980), the SNP site 3 (Scaffold720:596655), the SNP site 4 (Scaffold3614:66549), the SNP site 5 (Scaffold349:3413816), and the SNP site 6 (Scaffold920:281727) in each sample.

This method designed primers of different lengths for different mutation sites, after SNAPshot reaction, the products were analyzed by electrophoresis, five-color fluorescence detection, and Gene mapper analysis, and multiple SNP sites can be detected in one sequencing reaction. SNAPshot was used for site-specific sequence analysis, and the basic principle thereof followed the dideoxy termination method in direct DNA sequencing, except that only ddNTPs with different fluorescent labels were used in the PCR reaction. Since the 3'-end of the primers of each SNP site is close to the SNP point, each of the primers was extended by only one nucleotide according to the sequence of the template under the action of the polymerase. Then an advanced fluorescence detection system was used to detect the type of that nucleotide that is extended.

(1) Design of primers

Primers were designed and synthesized according to the position of Scaffold4239:309117 in the genome. In particular, Scaffold4239:309117 each extended 500 bp upstream and downstream. A nucleotide sequence thereof is shown as SEQ ID NO: 1 (FIG. 2, wherein N denotes the base to be tested at Scaffold4239:309117).

PCR primers:

```
                                          (SEQ ID NO: 2)
    F: GAAGACTAACCCGTATCGAG;

(SEQ ID NO: 3)
    R: ACACTTACAGTCTCTTGCGG.
```

Single base extension primer:

```
                                          (SEQ ID NO: 25)
ctgactgactgactgactgactATTGTCTCGTTGCTTCGGTTGTTTC.
```

Primers were designed and synthesized according to the position of Scaffold115:803980 in the genome. In particular, Scaffold115:803980 each extended 500 bp upstream and downstream. A nucleotide sequence thereof is shown as SEQ ID NO: 4 (wherein N denotes the base to be tested at Scaffold115:803980).

PCR primers:

```
                                          (SEQ ID NO: 5)
    F: CTTCATCTCCACCACACTTC;

(SEQ ID NO: 6)
    R: GCCCAAAGTAGCAAAGAGAG.
```

Single base extension primer:

```
                                          (SEQ ID NO: 26)
gactgactgactgactgactgactcaGCAGAGCTTGGCAAAGAGGGATG.
```

Primers were designed and synthesized according to the position of Scaffold720:596655 in the genome. In particular, Scaffold720:596655 each extended 500 bp upstream and downstream. A nucleotide sequence thereof is shown as SEQ ID NO: 7 (FIG. 4, wherein N denotes the base to be tested at Scaffold720:596655).

PCR primers:

```
    primer F:
                                          (SEQ ID NO: 8)
    CAACTTTGGTGATGACGGAC;

primer R:
                                          (SEQ ID NO: 9)
    TTCAACTGGTGTGTAGACGC.
```

Single base extension primer:

```
                                          (SEQ ID NO: 27)
gactgactgactgactagGCTACAGTTCGGACTCGAATTGTCAC.
```

Primers were designed and synthesized according to the position of Scaffold3614:66549 in the genome. In particular, Scaffold3614:66549 each extended 500 bp upstream and downstream. A nucleotide sequence thereof is shown as SEQ ID NO: 10 (FIG. 5, wherein N denotes the base to be tested at Scaffold3614:66549).

PCR primers:

```
                                          (SEQ ID NO: 11)
    F: GATGACACAACCCTCATCTG;

(SEQ ID NO: 12)
    R: AATGTATGCCCGGTAAGGAC.
```

Single base extension primer:

```
                                          (SEQ ID NO: 28)
    gactACTAACTTTACGCCCACGACCCA.
```

Primers were designed and synthesized according to the position of Scaffold349:3413816 in the genome. In particular, Scaffold349:3413816 each extended 500 bp upstream and downstream. A nucleotide sequence thereof is shown as SEQ ID NO: 13 (FIG. 6, wherein N denotes the base to be tested at Scaffold349:3413816).

PCR primers:

```
    primer F:
                                          (SEQ ID NO: 14)
    TCTCTGCACTGTTGTCACTC;

primer R:
                                          (SEQ ID NO: 15)
    CACCACACTTTCTTAGAAGG.
```

Single base extension primer:

```
                                          (SEQ ID NO: 29)
    actgactgactaAGGATCTAGTCCCTGCATAAATAACA.
```

Primers were designed and synthesized according to the position of Scaffold920:281727 in the genome. In particular, Scaffold920:281727 each extended 500 bp upstream and downstream. A nucleotide sequence thereof is shown as SEQ ID NO: 16 (FIG. 7, wherein N denotes the base to be tested at Scaffold920:281727).

PCR primers:

```
    primer F:
                                          (SEQ ID NO: 17)
    TTCGCATTCGTCCTTTTGGG;

primer R:
                                          (SEQ ID NO: 18)
    ACGTGCTACATTCTCCATCC.
```

Single base extension primer:

```
                                          (SEQ ID NO: 30)
tgactgactgactgactgactgactgactgactTAGCATCTAAGAAAGAG
GATTTA.
```

(2) PCR Amplification

PCR system (10 μl) was as follows:

| | |
|---|---|
| 2× Taq PCR Master Mix | 5 μl |
| PrimerMix (matching according to the amplification ratio) | 1 μl |

-continued

| | | |
|---|---|---|
| DNA template | 1 μl | |
| ddH₂O | 3 μl | |

PCR amplification procedure was as follows:

| | | |
|---|---|---|
| 95° C. | 5 minutes | |
| 95° C. | 30 seconds | ×45 cycles |
| 56° C. | 30 seconds | |
| 72° C. | 30 seconds | |
| 72° C. | 2 minutes | |
| 4° C. | forever | |

(3) PCR Product Purification

Purification was performed using shrimp alkaline phosphatase purification. The main functional components of shrimp alkaline phosphatase MIX (EX-SAP) are SAP and ExoI.SAP enzyme, which can dephosphorylate residual dNTPs, and ExoI degrades the free single-chain primer. 4 μl of PCR product was taken and added with 2 μl of EX-SAP enzyme. The specific reaction system is shown as follows:

| Constituent of digestive system | Volume (μl) |
|---|---|
| ddH₂O | 0.75 |
| SAP (1 U/ul) | 0.5 |
| ExoI (5 U/ul) | 0.15 |
| 10*SAP buffer | 0.6 |
| PCR product | 4 |
| Total volume | 6 |

After that, digestion and incubation were performed on a PCR instrument: 37° C. for 40 minutes, 85° C. for 5 minutes, 4° C. forever.

(4) SNAPshot Reaction

The PCR product was used as a template for SNAPshot reaction.

The SNAPshot reaction system is shown as follows:

| Reagent | Dosage (μl) |
|---|---|
| SNaPshot Mix | 0.5 |
| Pooled PCR Products | 3 |
| Pooled Primers | 1 |
| dH₂O | 0.5 |
| Total volume | 5 |

The SNAPshot reaction procedure is:

| | | |
|---|---|---|
| 95° C. | 2 minutes | |
| 95° C. | 10 seconds | ×40 cycles |
| 52° C. | 5 seconds | |
| 60° C. | 30 seconds | |
| 4° C. | forever | |

After that, the SNAPshot product was purified, and 2 μl of SAP mix was directly added to the SNAPshot reaction product. The specific reaction system was as follows:

| Constituent | Volume (μl) |
|---|---|
| Water | 0.9 |
| SAP(1 U/μl) | 0.5 |
| 10*SAP buffer | 0.6 |
| Total | 2 |

The SNAPshot product digestion reaction was performed on a PCR instrument, and the reaction procedures were: 37° C. for 40 minutes, 75° C. for 15 minutes, 4° C. forever.

(5) On-Machine Detection

2 μl of the digested SNAPshot reaction product was taken and added into 8 μl of deionized formamide containing 0.4% LIZ120, denatured at 95° C. for 5 minutes, then quenched at −20° C., and then sequenced on 3730XL.

(6) Result analysis

The .fsa results obtained by GeneMarker analysis were used to derive peak plots and table files, and to calculate the SNP mutant type of each sample II. Experimental Results Caffeine content and genotypes of SNP1, SNP2, SNP3, SNP4, SNP5, SNP6 sites of each sample are shown in Table 4, and the SNaPshot sequencing results of some samples are shown in FIG. 8 to FIG. 24.

TABLE 4

The CAF content in dry matter and genotype of the resource in the population:

| Sample | Caffeine content (%) | SNP1 genotype | SNP2 genotype | SNP3 genotype | SNP4 genotype | SNP5 genotype | SNP6 genotype |
|---|---|---|---|---|---|---|---|
| Sample 2-1 | 2.36 | GA | AA | CC | CT | AA | AA |
| Sample 2-2 | 2.89 | GA | AA | CC | CC | AA | AA |
| Sample 2-3 | 2.63 | GG | AA | CC | TT | AA | AA |
| Sample 2-4 | 3.38 | GG | AA | CC | TT | AA | AA |
| Sample 2-5 | 2.82 | GG | AA | CC | CT | AA | AA |
| Sample 2-6 | 2.24 | GG | AA | CC | TT | AA | AA |
| Sample 2-7 | 2.36 | GG | AA | CC | TT | AA | AA |
| Sample 2-8 | 2.18 | GG | AA | CC | TT | AA | AA |
| Sample 2-9 | 2.06 | GG | AA | CC | TT | AA | AA |
| Sample 2-10 | 2.93 | GG | AA | CC | TT | AA | AA |
| Sample 2-11 | 2.58 | AA | AA | CC | CT | AA | AA |
| Sample 2-12 | 2.52 | GG | AA | CC | TT | GA | AA |
| Sample 2-13 | 2.67 | GA | AA | CC | CT | AA | AA |
| Sample 2-14 | 0.12 | AA | AA | CC | CC | AA | AA |
| Sample 2-15 | 3.17 | GG | AA | CC | TT | AA | AA |

TABLE 4-continued

The CAF content in dry matter and genotype of the resource in the population:

| Sample | Caffeine content (%) | SNP1 genotype | SNP2 genotype | SNP3 genotype | SNP4 genotype | SNP5 genotype | SNP6 genotype |
|---|---|---|---|---|---|---|---|
| Sample 2-16 | 3.05 | GG | AA | CC | TT | AA | AA |
| Sample 2-17 | 2.51 | GG | AA | CC | TT | AA | AA |
| Sample 2-18 | 1.76 | AA | AA | CC | CT | AA | AA |
| Sample 2-19 | 3.06 | GG | AA | CC | TT | GA | AA |
| Sample 2-20 | 2.42 | AA | AA | CC | CT | AA | AA |
| Sample 2-21 | 2.73 | GG | AA | CC | TT | AA | AA |
| Sample 2-22 | 2.84 | GG | AA | CC | TT | AA | Not detected |
| Sample 2-23 | 2.54 | GG | AA | CC | TT | AA | AA |
| Sample 2-24 | 2.61 | GA | AA | CC | CT | AA | AA |
| Sample 2-25 | 2.82 | GG | AA | CC | TT | AA | AA |
| Sample 2-26 | 2.28 | GA | AA | CC | CT | AA | AA |
| Sample 2-27 | 2.20 | GA | GA | CC | TT | AA | AA |
| Sample 2-28 | 2.21 | GG | AA | CC | TT | AA | Not detected |
| Sample 2-29 | 2.16 | GG | AA | CC | TT | AA | AA |
| Sample 2-30 | 2.43 | GG | AA | CC | TT | AA | AA |
| Sample 2-31 | 1.67 | GG | AA | CC | TT | AA | AA |
| Sample 2-32 | 2.10 | GG | AA | CC | TT | GA | Not detected |
| Sample 2-33 | 1.95 | GG | AA | CC | TT | AA | AA |
| Sample 2-34 | 2.46 | GG | AA | CC | TT | AA | AA |
| Sample 2-35 | 2.80 | GG | AA | CC | TT | AA | AA |
| Sample 2-36 | 2.31 | GG | AA | CC | TT | GA | AA |
| Sample 2-37 | 2.79 | GA | AA | CC | TT | AA | AA |
| Sample 2-38 | 2.19 | GG | AA | CC | CC | GA | Not detected |
| Sample 2-39 | 2.08 | GA | AA | CC | TT | AA | AA |
| Sample 2-40 | 2.72 | GA | AA | CC | TT | AA | AA |
| Sample 2-41 | 3.10 | GG | AA | CC | TT | AA | AA |
| Sample 2-42 | 2.99 | GG | AA | CC | TT | AA | AA |
| Sample 2-43 | 2.12 | GA | AA | CC | TT | AA | AA |
| Sample 2-44 | 2.94 | AA | AA | CC | CT | AA | AA |
| Sample 2-45 | 2.76 | GG | AA | CC | TT | GA | Not detected |
| Sample 2-46 | 3.01 | GA | GA | CC | TT | AA | AA |
| Sample 2-47 | 2.21 | GG | AA | CC | TT | AA | AA |
| Sample 2-48 | 2.75 | GG | AA | CC | TT | AA | Not detected |
| Sample 2-49 | 2.12 | GG | AA | CC | TT | GA | AA |
| Sample 2-50 | 2.67 | GG | GA | CC | TT | AA | AA |
| Sample 2-51 | 2.24 | GA | AA | CC | TT | AA | AA |
| Sample 2-52 | 2.56 | GG | AA | CC | TT | AA | AA |
| Sample 2-53 | 3.29 | GG | AA | CC | TT | AA | AA |
| Sample 2-54 | 3.06 | GG | AA | CC | TT | AA | AA |
| Sample 2-55 | 2.43 | GG | AA | CC | TT | AA | AA |
| Sample 2-56 | 2.63 | GG | AA | CC | TT | AA | AA |
| Sample 2-57 | 2.74 | GG | AA | CC | TT | AA | AA |
| Sample 2-58 | 2.74 | GG | AA | CC | TT | AA | AA |
| Sample 2-59 | 3.24 | GG | AA | CC | TT | AA | AA |
| Sample 2-60 | 3.29 | GG | AA | CC | TT | AA | AA |
| Sample 2-61 | 2.63 | GG | AA | CC | TT | AA | AA |
| Sample 2-62 | 2.92 | GG | AA | CC | TT | AA | AA |
| Sample 2-63 | 1.65 | AA | AA | CC | TT | AA | AA |
| Sample 2-64 | 1.44 | GG | AA | CC | TT | AA | AA |
| Sample 2-65 | 1.94 | GG | AA | CT | TT | AA | Not detected |
| Sample 2-66 | 2.38 | GG | AA | CC | TT | GG | AA |
| Sample 2-67 | 2.52 | GG | AA | CC | TT | AA | AA |
| Sample 2-68 | 2.42 | GG | AA | CC | TT | GA | AA |
| Sample 2-69 | 2.48 | GG | AA | CC | CT | AA | AA |
| Sample 2-70 | 2.61 | GG | AA | CC | TT | AA | Not detected |
| Sample 2-71 | 2.94 | GG | AA | CC | TT | AA | AA |
| Sample 2-72 | 2.12 | GA | AA | CC | CT | AA | AA |
| Sample 2-73 | 2.66 | GA | AA | CC | CT | AA | AA |
| Sample 2-74 | 2.45 | GG | AA | CC | TT | AA | Not detected |
| Sample 2-75 | 2.41 | AA | AA | CC | CT | AA | AA |
| Sample 2-76 | 2.57 | GG | AA | CC | TT | AA | AA |
| Sample 2-77 | 2.64 | GA | GA | CT | CC | GG | GG |
| Sample 2-78 | 2.17 | GG | AA | CC | TT | AA | AA |
| Sample 2-79 | 1.88 | GG | AA | CC | TT | AA | AA |
| Sample 2-80 | 2.01 | GA | GA | CC | TT | AA | AA |
| Sample 2-81 | 2.44 | GG | AA | CC | TT | AA | AA |
| Sample 2-82 | 2.26 | GG | AA | CC | TT | AA | AA |
| Sample 2-83 | 2.39 | GA | AA | CC | TT | AA | AA |
| Sample 2-84 | 2.39 | GG | AA | CC | TT | AA | AA |
| Sample 2-85 | 2.95 | GG | AA | CC | CT | AA | AA |
| Sample 2-86 | 2.86 | GA | AA | CC | TT | AA | AA |
| Sample 2-87 | 2.87 | GA | AA | CC | TT | AA | AA |
| Sample 2-88 | 3.04 | GA | AA | CC | TT | AA | AA |
| Sample 2-89 | 3.28 | GA | AA | CC | TT | AA | AA |

TABLE 4-continued

The CAF content in dry matter and genotype of the resource in the population:

| Sample | Caffeine content (%) | SNP1 genotype | SNP2 genotype | SNP3 genotype | SNP4 genotype | SNP5 genotype | SNP6 genotype |
|---|---|---|---|---|---|---|---|
| Sample 2-90 | 3.16 | GG | AA | CC | TT | AA | AA |
| Sample 2-91 | 2.09 | GG | AA | CC | TT | AA | AA |
| Sample 2-92 | 2.85 | GG | AA | CC | TT | AA | Not detected |
| Sample 2-93 | 2.63 | GG | AA | CC | TT | AA | AA |
| Sample 2-94 | 1.02 | GG | AA | CC | CT | AA | GA |
| Sample 2-95 | 3.21 | GG | AA | CC | CT | GA | AA |
| Sample 2-96 | 2.30 | GG | AA | CC | TT | AA | AA |
| Sample 2-97 | 0.07 | AA | GG | CT | CC | GG | GG |
| Sample 2-98 | 0.08 | AA | GA | CT | CC | GG | GG |

The significance analysis results show that the genotype of Scaffold4239:309117 is extremely significantly correlated with caffeine content, the correlation coefficient is −0.4, p-value is $3.66 \times 10^{-5}$, F-value (6.91/3.94) is 18.7, which is a recessive mutation, and the caffeine content in the dry matter of tea soup corresponding to an AA genotype sample has extremely significant difference compared with GG and GA genotype samples. It is statistically judged that, when the genotype sample is double mutant AA, the caffeine content in the dry matter in the tea plant is more likely to be lower than the normal average of the sample of which the genotype is wild type GG or single mutant GA.

The significance analysis results show that, the genotype of Scaffold115:803980 is extremely significantly correlated with caffeine content, the correlation coefficient is −0.4, p-value is $3.66 \times 10^{-5}$, F-value (6.91/3.94) is 18.7, which is a recessive mutation, and the caffeine content in the dry matter of the tea plant corresponding to a GG genotype sample has extremely significant difference compared with AA and GA genotype samples. It is statistically judged that, when the genotype of the sample is double mutant GG, the caffeine content in the dry matter in the tea plant is more likely to be lower than the normal average of the sample of which the genotype is wild type AA or single mutant GA.

The significance analysis results show that, the genotype of Scaffold720:596655 is extremely significantly correlated with caffeine content, the correlation coefficient is −0.51, p-value is $5.78 \times 10^{-6}$, F-value (6.91/3.94) is 23.1, which is a dominant mutation, the caffeine content in the dry matter of the tea plant corresponding to a wild type CC genotype sample has significant difference compared with a single mutant CT genotype sample. It is statistically judged that, when the genotype of the sample is single mutant CT genotype, the caffeine content in the dry matter in the tea plant is more likely to be lower than the normal average of the sample with wild type CC genotype.

The significance analysis results show that, the genotype of Scaffold3614:66549 is extremely significantly correlated with caffeine content, the correlation coefficient is −0.48, p-value is $5.45 \times 10^{-7}$, F-value (6.91/3.94) is 28.9, which is a recessive mutation, and the caffeine content in the dry matter of tea soup corresponding to a CC genotype sample has significant difference compared with TT and CT genotype samples. It is statistically judged that, when the genotype is double mutant CC, the caffeine content in the dry matter in the tea plant is more likely to be lower than the normal average of the sample of which the genotype is wild type TT or single mutant CT.

The significance analysis results show that, the genotype of Scaffold349:3413816 is extremely significantly correlated with caffeine content, the correlation coefficient is −0.4, p-value is $-4.04 \times 10^{-5}$, F-value (6.91/3.94) is 18.5, which is a recessive mutation, the caffeine content in the dry matter of tea soup corresponding to a GG genotype sample has significant difference compared with GA and AA genotype samples. It is statistically judged that, when the genotype is double mutant GG, the caffeine content in the dry matter in the tea plant is more likely to be lower than the normal average of the sample of which the genotype is wild type AA or single mutant GA.

The significance analysis results show that, the genotype of Scaffold920:281727 is extremely significantly correlated with caffeine content, the correlation coefficient is −0.45, p-value is $3.16 \times 10^{-6}$, F-value (6.91/3.94) is 18.7, which is a recessive mutation, the caffeine content in the dry matter of tea soup corresponding to a GG genotype sample has significant difference compared with GA and AA genotype samples. It is statistically judged that, when the genotype is double mutant GG, the caffeine content in the dry matter in the tea plant is more likely to be lower than the normal average of the sample of which the genotype is wild type AA or single mutant GA.

Embodiment 3 Kit for Evaluating Tea Plant Caffeine Content

I. Composition

The primers for the SNP site 1 which have the nucleotide sequence shown as SEQ ID NO: 2 and SEQ ID NO: 3, the primers for the SNP site 2 which have the nucleotide sequence shown as SEQ ID NO: 5 and SEQ ID NO: 6, the primers for the SNP site 3 which have the nucleotide sequence shown as SEQ ID NO: 8 and SEQ ID NO: 9, the primers for the SNP site 4 which have the nucleotide sequence shown as SEQ ID NO: 11 and SEQ ID NO: 12, the primers for the SNP site 5 which have the nucleotide sequence shown as SEQ ID NO: 14 and SEQ ID NO: 15, the primers for the SNP site 6 which have the nucleotide sequence shown as SEQ ID NO: 17 and SEQ ID NO: 18, 2×Taq PCR Master Mix, ddH$_2$O.

```
In particular, primer F for SNP site 1:
                                   (SEQ ID NO: 2)
GAAGACTAACCCGTATCGAG;

primer R for SNP site 1:
                                   (SEQ ID NO: 3)
ACACTTACAGTCTCTTGCGG;

primer F for SNP site 2:
```

```
                                                       (SEQ ID NO: 5)
CTTCATCTCCACCACACTTC;

primer R for SNP site 2:
                                                       (SEQ ID NO: 6)
GCCCAAAGTAGCAAAGAGAG;

primer F for SNP site 3:
                                                       (SEQ ID NO: 8)
CAACTTTGGTGATGACGGAC;

primer R for SNP site 3:
                                                       (SEQ ID NO: 9)
TTCAACTGGTGTGTAGACGC;

primer F for SNP site 4:
                                                       (SEQ ID NO: 11)
GATGACACAACCCTCATCTG;

primer R for SNP site 4:
                                                       (SEQ ID NO: 12)
AATGTATGCCCGGTAAGGAC;

primer F for SNP site 5:
                                                       (SEQ ID NO: 14)
TCTCTGCACTGTTGTCACTC;

primer R for SNP site 5:
                                                       (SEQ ID NO: 15)
CACCACACTTTCTTAGAAGG;

primer F for SNP site 6:
                                                       (SEQ ID NO: 17)
TTCGCATTCGTCCTTTTGGG;

primer R for SNP site 6:
                                                       (SEQ ID NO: 18)
ACGTGCTACATTCTCCATCC.
```

II. Usage method (1) The CTAB method was used to extract total DNA from buds of tea plant, and it was ensured that A260/A280 of each DNA sample is between 1.8 and 2.0, and the concentration was greater than 100 μg/μl.

(2) PCR Amplification

Detection primers with nucleotide sequences shown as SEQ ID NO: 2 and SEQ ID NO: 3, SEQ ID NO: 5 and SEQ ID NO: 6, SEQ ID NO: 8 and SEQ ID NO: 9, SEQ ID NO: 11 and SEQ ID NO: 12, SEQ ID NO: 14 and SEQ ID NO: 15 and SEQ ID NO: 17 and SEQ ID NO: 18 were used for detecting SNP site 1, SNP site 2, SNP site 3, SNP site 4, SNP site 5 and SNP site 6, respectively.

PCR system (10 μl) was as follows:

| 2× Taq PCR Master Mix | 5 μl |
|---|---|
| primer | Each 0.5 μl |
| DNA template | 1 μl |
| ddH$_2$O | 3 μl |

PCR amplification procedure was as follows:

| 95° C. | 5 minutes | |
|---|---|---|
| 95° C. | 30 seconds | ×45 cycles |
| 56° C. | 30 seconds | |
| 72° C. | 30 seconds | |
| 72° C. | 2 minutes | |
| 4° C. | forever | |

(3) Product Purification

The PCR amplification products were subjected to gel electrophoresis, followed by recovery and purification using a commercially available gel electrophoresis DNA recovery kit.

A band with a fragment length of about 240 bp in the amplification product of the primers shown in SEQ ID NO: 2 and SEQ ID NO: 3 was selected for recovery and purification.

A band with a fragment length of about 240 bp in the amplification product of the primers shown in SEQ ID NO: 5 and SEQ ID NO: 6 was selected for recovery and purification.

A band with a fragment length of about 250 bp in the amplification product of the primers shown in SEQ ID NO: 8 and SEQ ID NO: 9 was selected for recovery and purification.

A band with a fragment length of about 240 bp in the amplification product of the primers shown in SEQ ID NO: 11 and SEQ ID NO: 12 was selected for recovery and purification.

A band with a fragment length of about 240 bp in the amplification product of the primers shown in SEQ ID NO: 14 and SEQ ID NO: 15 was selected for recovery and purification.

(4) Sequencing and Interpretation of Results

The amplification products of the primers shown in SEQ ID NO: 2 and SEQ ID NO: 3 were recovered and purified and sent to a sequencing company for Sanger sequencing. The sequencing results were compared with the nucleotide sequence shown in SEQ ID NO: 1. According to FIG. 2 (bold and underlined parts denote upstream and downstream primers), the site Scaffold4239:309117 is located at the 73rd base of the amplification product. It is statistically judged that, when the genotype sample is double mutant AA, the caffeine content in the dry matter in the tea plant is more likely to be lower than the normal average of the sample of which the genotype is wild type GG or single mutant GA.

The amplification products of the primers shown in SEQ ID NO: 5 and SEQ ID NO: 6 were recovered and purified and sent to a sequencing company for Sanger sequencing. The sequencing results were compared with the nucleotide sequence shown in SEQ ID NO: 4. According to FIG. 3 (bold and underlined parts denote upstream and downstream primers), the site Scaffold115:803980 is located at the 164th base of the amplification product. It is statistically judged that, when the genotype of the sample is double mutant GG, the caffeine content in the dry matter in the tea plant is more likely to be lower than the normal average of the sample of which the genotype is wild type AA or single mutant GA.

The amplification products of the primers shown in SEQ ID NO: 8 and SEQ ID NO: 9 were recovered and purified and sent to a sequencing company for Sanger sequencing. The sequencing results were compared with the nucleotide sequence shown in SEQ ID NO: 7. According to FIG. 4 (bold and underlined parts denote upstream and downstream primers), the site Scaffold720:596655 is located at the 189th base of the amplification product. It is statistically judged that, when the genotype of the sample is single mutant CT genotype, the caffeine content in the dry matter in the tea plant is more likely to be lower than the normal average of the sample with wild type CC genotype.

The amplification products of the primers shown in SEQ ID NO: 11 and SEQ ID NO: 12 were recovered and purified and sent to a sequencing company for Sanger sequencing. The sequencing results were compared with the nucleotide sequence shown in SEQ ID NO: 10. According to FIG. 5 (bold and underlined parts denote upstream and downstream primers), the site Scaffold3614:66549 is located at the 137th base of the amplification product. It is statistically judged that, when the genotype is double mutant CC, the caffeine content in the dry matter in the tea plant is more likely to be lower than the normal average of the sample of which the genotype is wild type TT or single mutant CT.

The amplification products of the primers shown in SEQ ID NO: 14 and SEQ ID NO: 15 were recovered and purified and sent to a sequencing company for Sanger sequencing. The sequencing results were compared with the nucleotide sequence shown in SEQ ID NO: 13. According to FIG. 6 (bold and underlined parts denote upstream and downstream primers), the site Scaffold349:3413816 is located at the 160th base of the amplification product. It is statistically judged that, when the genotype is double mutant GG, the caffeine content in the dry matter in the tea plant is more likely to be lower than the normal average of the sample of which the genotype is wild type AA or single mutant GA.

The amplification products of the primers shown in SEQ ID NO: 17 and SEQ ID NO: 18 were recovered and purified and sent to a sequencing company for Sanger sequencing. The sequencing results were compared with the nucleotide sequence shown in SEQ ID NO: 16. According to FIG. 7 (bold and underlined parts denote upstream and downstream primers), the site Scaffold920:281727 is located at 106th base of the amplification product. It is statistically judged that, when the genotype is double mutant GG, the caffeine content in the dry matter in the tea plant is more likely to be lower than the normal average of the sample of which the genotype is wild type AA or single mutant GA Embodiment 4 Use of Kit for Evaluating Tea Plant Caffeine Content I. Experimental Method The kit in Embodiment 3 was used to detect 98 tea plant samples in Embodiment 2.

II. Experiment Results

The detection results are consistent with those of Embodiment 2 using the SnaPShot technology platform. This kit can be used to evaluate the tea plant caffeine content. The sequencing peaks of some samples are shown in FIG. 25 to FIG. 29.

What is claimed is:

1. A method for evaluating tea plant caffeine content, comprising detecting a genotype of a molecular marker by using primers, wherein the primers consist of nucleotide sequences shown as SEQ ID NO: 8 and SEQ ID NO: 9,
wherein the molecular marker is a SNP site 3, wherein the SNP site 3 is located at position 501 of the nucleotide sequence of SEQ ID NO: 7,
when a genotype of a sample is single mutant CT, the caffeine content in the dry matter in the tea plant is more likely to be lower than the normal average of the sample of which the genotype is double mutant CC.

* * * * *

SEQUENCE LISTING

```
<160> NUMBER OF SEQ ID NOS: 30

<210> SEQ ID NO 1
<211> LENGTH: 1001
<212> TYPE: DNA
<213> ORGANISM: Camellia sinensis
<220> FEATURE:
<221> NAME/KEY: misc_feature
<222> LOCATION: (501)..(501)
<223> OTHER INFORMATION: n is a, c, g, or t

<400> SEQUENCE: 1
gaaggctctg gagtagctga agttgttatg agcttgtcta ggccgaaatc agcgaggtga      60
gcttcaaaat cggcgtcgaa taggacgttc tgaggcttga catcgccatg aaccatggcg     120
gtggagtgga ggaaggcgag gccgcgggcg attccgaggg ctattaggtg gcgcattggc     180
caattcaata catgcccgtc ttggtgagaa gcttcttgaa gcaatgtggc taggtttccg     240
ttaggcatat agtcgtagac taagagtctg aggtctggtg gtccggcgaa gtacccacgg     300
aggactgtga ggtttctgtg cttcactctc ccgagcgatt cggcttcttt tctgaacatg     360
ttttcgtcta gcgatccatc agggagtctc cgaatcgaaa gcaccattcc atcactgtaa     420
caggctttga agactaaccc gtatcgagtc ctgcttagaa cgttctcttc atcgaattgt     480
ctcgttgctt cggttgtttc ngctagagtg atcttgttat tgaacataac aagctttgga     540
ccgccattat cgccacttcc acgacctccg ctggctgcag ctgagcttgc tcttgctggg     600
ctgcgctttt tctctccggc agccttttct ttgagcctct tgcgccaccg caagagactg     660
taagtgtaga agcaacaaca cagtgctaag aggaaaccac cactaacagc catggcaata     720
aacatgatca gcctcttctt cctattactc atctcttcgc atttcgtgct taagggtttc     780
ccacataagt tcggatttcc tgcataatca gatggatcgt tgaatcttga agccagcatt     840
gttggaatct cgccggagag gttgttttgg gatacattga agtagaccaa gctagagatg     900
agtgaaatgt ttgctggaat cggtccggtc aggttgtttg cagagagatt gaggactgtg     960
aggtttgata aattggacaa tgagtctggt atttggcctg g                        1001

<210> SEQ ID NO 2
<211> LENGTH: 20
<212> TYPE: DNA
<213> ORGANISM: Camellia sinensis
```

<400> SEQUENCE: 2
gaagactaac ccgtatcgag                                              20

<210> SEQ ID NO 3
<211> LENGTH: 20
<212> TYPE: DNA
<213> ORGANISM: Camellia sinensis

<400> SEQUENCE: 3
acacttacag tctcttgcgg                                              20

<210> SEQ ID NO 4
<211> LENGTH: 1001
<212> TYPE: DNA
<213> ORGANISM: Camellia sinensis
<220> FEATURE:
<221> NAME/KEY: misc_feature
<222> LOCATION: (501)..(501)
<223> OTHER INFORMATION: n is a, c, g, or t

<400> SEQUENCE: 4
aatcattaag agtcattatg gtaatcatga gcttaattac tccaagtaaa gccaatcttc    60
atcatagaaa taaaaattac aaaaaaaaaa aaaaaaaaa agtctttcag ctgaacaacc   120
catccctgca actgcaccac cataattgag atctaaatct gaaggaactt gcttgagatc   180
taaatctgaa ggaacttgct tgcttaggaa catccacatc catgatttct acaattttg    240
gaagacacag aaccagagaa gatgactcaa atcaagcag caattgtaag aaaattcgac    300
caatcgaaat catcttggaa ttaatcattg tagcctcctt catctccacc acacttctcc   360
tcctacttcc atgcgattac gtcgacggca gccctattcc caccatcata ttcaaaggac   420
tccccctccac cttccacgcc ttcgtcgtct ccctcatctt cgccttctcc ggagccttga   480
gcgccttgtt gatccacgac ncatccctct ttgccaagct ctgcgagttc tcttccatgg   540
cctccatgac ctctgctctc tctttgctac tttgggctat gttcttcacc tgttttcaac   600
cacaacccag gtaaaactcg aattcagaca tcacatggta agaaaacaag ttattaaggt   660
ttttaacctt ataaagactt ttttctttt ttcttttcct tcctgtccaa cggacacgtg   720
gtgtgtttta aaattaataa atcgtgtatc agatatggat atacaatcgc gtggtcagtt   780
gaaattacta ttggtatgct ttatataccg tgtcgtgtgt aaaattaaaa cttgttttgt   840
gatgttgttg gtctgttatg tacttggtgt tgttgaaata atattaccat aaatttgaat   900
aagcctttat tatgtggaga tccgatggat taatgatgca tattgtcaca gaattcaaaa   960
tgatttcatt ttgagcatgg tgacgagggt tccaagccct g                     1001

<210> SEQ ID NO 5
<211> LENGTH: 20
<212> TYPE: DNA
<213> ORGANISM: Camellia sinensis

<400> SEQUENCE: 5
cttcatctcc accacacttc                                              20

<210> SEQ ID NO 6
<211> LENGTH: 20
<212> TYPE: DNA
<213> ORGANISM: Camellia sinensis

<400> SEQUENCE: 6

```
gcccaaagta gcaaagagag                                               20
```

<210> SEQ ID NO 7
<211> LENGTH: 1001
<212> TYPE: DNA
<213> ORGANISM: Camellia sinensis
<220> FEATURE:
<221> NAME/KEY: misc_feature
<222> LOCATION: (501)..(501)
<223> OTHER INFORMATION: n is a, c, g, or t

<400> SEQUENCE: 7

```
gcccactaga taatggcaaa accatctttt ctaaagccca cttgagggtg gcaaaatctg    60
cattttagcc tacttgcgag tagcaaacca ttttcagaac aaacatgaaa tgttttgttc   120
caatttaggc gatttggtct acacttgttt gctgtgcgca taacatagta attctaggct   180
aataaccgga ataaaagcat ataatgtttt caaaacaaga tatcatggtt agtagaggcc   240
gatctttgat cgggcgagtg ggtatgctca tagctgacct gccccaattg tacccaagtt   300
cccgagccga gacaactttg gtgatgacgg acacgtgccc tttggcaccg agtcagggtt   360
tcttaaattc tcccaaaata aaatatttag gtggcgactc tgtatctggc aaagcagtcc   420
atgtttggca cttcttttct aaaaatctgt tttctcaaaa caatttgccg gatttggact   480
ctttggttca gattaagaac ngtgacaatt cgagtccgaa ctgtagcatg gggcccacgg   540
gcgcgtctac acaccagttg aaggtaaaga cagaagatgt tgagaaaatt gcattcagag   600
cgaggtatgg tcattatgaa ttccttgtta tgccatttgg agtaactaat gcccctgcaa   660
cgtttataga cctaatgaac tgtattttta agacttatct tgatgatttt gttgtgattt   720
tattaatgat atcttggtgt attcaaagaa tagacttgaa catgaacacc acttgagaac   780
tttcttgcaa acacttaaag aaaagaaatt attttccaaa ctaaaaaaat gtgaattttg   840
gttggatgaa gtcattttct tagggcatgt tatcaacaag gaagaaattt cagtagatcc   900
acagaaaatt gaagcaattg tgaattgacc cactccaaca aatataacag aagtccatag   960
tttcgtgggc ttagctgggt actacagaag atttgtgaag g                      1001
```

<210> SEQ ID NO 8
<211> LENGTH: 20
<212> TYPE: DNA
<213> ORGANISM: Camellia sinensis

<400> SEQUENCE: 8

```
caactttggt gatgacggac                                               20
```

<210> SEQ ID NO 9
<211> LENGTH: 20
<212> TYPE: DNA
<213> ORGANISM: Camellia sinensis

<400> SEQUENCE: 9

```
ttcaactggt gtgtagacgc                                               20
```

<210> SEQ ID NO 10
<211> LENGTH: 1001
<212> TYPE: DNA
<213> ORGANISM: Camellia sinensis
<220> FEATURE:
<221> NAME/KEY: misc_feature
<222> LOCATION: (501)..(501)
<223> OTHER INFORMATION: n is a, c, g, or t

<400> SEQUENCE: 10

```
gagtcatggg tttcttaaat ttctctaaaa aatatttagg tggtgactct gtatctggca      60
aaatagtcca tttttggcaa tttgattcaa atcagttttt ccaacatatt tgccgaattg     120 ggacttttg gtgattatct atttcacatt gcacatgtga aatcagattc agaaccgtgg      180
gagtccgata ctgtagggct tattcgtctt ccgaaagggg gcatgcaaag tcgaactaca    240
agtcccctgg ggaggatgga ttgcaaaatt accgtacaca gtagcaatcc cgtctttaaa    300
ggcgtacttt accaactgat ggaccattga tgacacaacc ctcatctgat gtagccaggg    360
tcttcccagt agtagattga aagtgtccga acatccatg acatagaatt taacctgatg     420
ctcagacggg ccgagtagga tatggctctt aaacattacc atgacatctt ggctcgtatt    480
gtcatataag cctaaacggc ntgggtcgtg ggcgtaaagt tagtcggcct cacaccgatg    540
gcataggcgg tccttaccgg gcatacatta atcgccgatc cgttatctac caacaccact    600
ggaatccact ttttctgact ttccagcgtt acatataagg gccaattgtg gttagcaccc    660
tcaggtggta actctttatc tataaaagat atcactggcg taacatcccc ggatgtaacc    720
aatgatacca attggtcagc agtggtttcg atagggagtt tggtccggtt cattgcctct    780
agcagcagtg cctgtctatg ctcccgagat gccatgatta gccccagat tgatatgtcg     840 gcctgaatct tcttaagctg tttcaagacc aggttttctt caacatcctt ctcttttgat    900
ttctcgaccc ccactgtcct tgatatatgc catcttttag ggttatcacc cattggtacc    960
cctttcggtc tagattaccc tgactttaag gtctccttct c                        1001

<210> SEQ ID NO 11
<211> LENGTH: 20
<212> TYPE: DNA
<213> ORGANISM: Camellia sinensis

<400> SEQUENCE: 11
gatgacacaa ccctcatctg                                                 20

<210> SEQ ID NO 12
<211> LENGTH: 20
<212> TYPE: DNA
<213> ORGANISM: Camellia sinensis

<400> SEQUENCE: 12
aatgtatgcc cggtaaggac                                                 20

<210> SEQ ID NO 13
<211> LENGTH: 1001
<212> TYPE: DNA
<213> ORGANISM: Camellia sinensis
<220> FEATURE:
<221> NAME/KEY: misc_feature
<222> LOCATION: (501)..(501)
<223> OTHER INFORMATION: n is a, c, g, or t

<400> SEQUENCE: 13
ataatctttt tgtacttgtt caggtggaat gaagcaatca accgagagtc caggaacatt    60
gaatgctagg tcgtcgatct tccaagtctc ctccatccgt gtgattgctg tgcccgctct   120
cagattgtcc ccaaatcttg agatgatcac acttgattgg ccagaatgcg cgatcatcgt   180
gccctccacc atccgatagt cctcgatttt cgtgcccatg gtggtctccc aataggtagg   240
gtaggttccg ggggactgga ttctggtgag gtaagagtcc tctaaataca ctagcagacc   300
acttctttgg ctgaagtaac caaacatgac atgcttgatc atctctgcac tgttgtcact   360
```

```
ccgatcggct aggtccgtct gatccgcgga caatttcaac acgaagcaat cgacgctcaa      420
gattcgtttt tcgcccacgt attgtgctag ggaaaacaca gccgatacag ccacaggatc      480
tagtccctgc ataaataaca ntatgttttt tacatagagg aaaataatat ctgtcacatg      540
aattctactc catttttaa ccttctaaga agtgtggtg aaaaaatat taaatccatt         600 gggtaaaata taacagtctt taacataaca atatggcgaa ctatacattc aattctagaa      660
aatgtctcat ttttatagat ttttatgaaa gggatcaacc ttcttttttt ttattggaag      720
cactatataa ataatgtcaa atagttttcc aaacttatct aaataaagtt ttaataattt      780
taatccacac atttttgaatt taatttactt attttttagta gataacatta ccacagtcaa    840
aaagagtgcc aacatgaacc tccagcacac ttgaagagca cttgacgatc atattgggaa      900
agttaccagc cagcactccc aaaaaaaaaa aagaaaaaa agataaaaga ttaaaaaaat       960
tagtaaaaag tgactttaca aaaggaata ttccacctct g                          1001
```

<210> SEQ ID NO 14
<211> LENGTH: 20
<212> TYPE: DNA
<213> ORGANISM: Camellia sinensis

<400> SEQUENCE: 14

```
tctctgcact gttgtcactc                                                   20
```

<210> SEQ ID NO 15
<211> LENGTH: 20
<212> TYPE: DNA
<213> ORGANISM: Camellia sinensis

<400> SEQUENCE: 15

```
caccacactt tcttagaagg                                                   20
```

<210> SEQ ID NO 16
<211> LENGTH: 1001
<212> TYPE: DNA
<213> ORGANISM: Camellia sinensis
<220> FEATURE:
<221> NAME/KEY: misc_feature
<222> LOCATION: (501)..(501)
<223> OTHER INFORMATION: n is a, c, g, or t

<400> SEQUENCE: 16

```
agggagactt ttatcttgag agctagaaga agagaaagtt agagaaaaga aagagaagta      60
ggaagaaaat caaagggaat tcacattcgt cctttggag ttgagaattg aacacttagg      120
tgatttcgaa aatcataaat gaggtgtgtt aaactaatat cgttcagcta cagttactca     180
gtaaattctc tttctcagag gctacgcagg tgtagtttga gttaaacttg gccacttaaa     240
ctaatggaac cattagggc ccaagctaat tagttcctag aacaaggag agaggacgga       300 gaagcataga gaaagttaga gagaaacttt tttcttgaga gatagaagag atagttagag    360
aaaagaaaga gaaacgggaa aaaaatcatt gggaattcgc attcgtcctt ttgggcttga    420
gaattgaaca gttggggaat ttgggaaacc ttaaatgcgg tgcttatgtt taactaatat    480
cgttaagtgc caattactca ntaaatcctc tttcttagat gctaagcaag atttagtgta    540
gttaaacttg gccacttaag ctaatggaac agttagggtc ccaagcgaat tagtttccta    600
gaacaaaaga tagaaggatg gagaaatgtag cacgttcgtg agggaccccg ctactacagt    660
tcggactcga tttgtgtcac ggttcttaat ctgaaccaaa gagtccaaat ccggcaaatc    720
gttttgagaa acagattttt tgaaaagaag tgccaaacat ggactgcttt gctagatata    780
```

```
gagtcgccac ctaaatattt ttttaaaatg gggaaattta ggaaaccta acttggtgcc      840 aaaggccacg tgtccgtcat tgccaaagtt gcctgggctc gggagcttgg gtacgattgg     900
ggaaggtcag ctatgagcac cccctctcgc ccgatccgaa gatcggcctc tactaaccgt     960
gatatccgtt tttgaaaacg ttatgtgttc ttaaaccaat t                         1001

<210> SEQ ID NO 17
<211> LENGTH: 20
<212> TYPE: DNA
<213> ORGANISM: Camellia sinensis

<400> SEQUENCE: 17
ttcgcattcg tccttttggg                                                  20

<210> SEQ ID NO 18
<211> LENGTH: 20
<212> TYPE: DNA
<213> ORGANISM: Camellia sinensis

<400> SEQUENCE: 18
acgtgctaca ttctccatcc                                                  20

<210> SEQ ID NO 19
<211> LENGTH: 20
<212> TYPE: DNA
<213> ORGANISM: Camellia sinensis

<400> SEQUENCE: 19
ccgcaagaga ctgtaagtgt                                                  20

<210> SEQ ID NO 20
<211> LENGTH: 20
<212> TYPE: DNA
<213> ORGANISM: Camellia sinensis

<400> SEQUENCE: 20
ctctctttgc tactttgggc                                                  20

<210> SEQ ID NO 21
<211> LENGTH: 20
<212> TYPE: DNA
<213> ORGANISM: Camellia sinensis

<400> SEQUENCE: 21
gcgtctacac accagttgaa                                                  20

<210> SEQ ID NO 22
<211> LENGTH: 20
<212> TYPE: DNA
<213> ORGANISM: Camellia sinensis

<400> SEQUENCE: 22
gtccttaccg ggcatacatt                                                  20

<210> SEQ ID NO 23
<211> LENGTH: 20
<212> TYPE: DNA
<213> ORGANISM: Camellia sinensis

<400> SEQUENCE: 23
ccttctaaga aagtgtggtg                                                  20
```

<210> SEQ ID NO 24
<211> LENGTH: 20
<212> TYPE: DNA
<213> ORGANISM: Camellia sinensis

<400> SEQUENCE: 24
ggatggagaa tgtagcacgt                                                   20

<210> SEQ ID NO 25
<211> LENGTH: 47
<212> TYPE: DNA
<213> ORGANISM: Camellia sinensis

<400> SEQUENCE: 25
ctgactgact gactgactga ctattgtctc gttgcttcgg ttgtttc                     47

<210> SEQ ID NO 26
<211> LENGTH: 49
<212> TYPE: DNA
<213> ORGANISM: Camellia sinensis

<400> SEQUENCE: 26
gactgactga ctgactgact gactcagcag agcttggcaa agagggatg                   49

<210> SEQ ID NO 27
<211> LENGTH: 44
<212> TYPE: DNA
<213> ORGANISM: Camellia sinensis

<400> SEQUENCE: 27
gactgactga ctgactaggc tacagttcgg actcgaattg tcac                        44

<210> SEQ ID NO 28
<211> LENGTH: 27
<212> TYPE: DNA
<213> ORGANISM: Camellia sinensis

<400> SEQUENCE: 28
gactactaac tttacgccca cgaccca                                           27

<210> SEQ ID NO 29
<211> LENGTH: 38
<212> TYPE: DNA
<213> ORGANISM: Camellia sinensis

<400> SEQUENCE: 29
actgactgac taaggatcta gtccctgcat aaataaca                               38

<210> SEQ ID NO 30
<211> LENGTH: 56
<212> TYPE: DNA
<213> ORGANISM: Camellia sinensis

<400> SEQUENCE: 30
tgactgactg actgactgac tgactgactg acttagcatc taagaaagag gattta           56